US012332117B2

(12) United States Patent
Vercauteren et al.

(10) Patent No.: US 12,332,117 B2
(45) Date of Patent: Jun. 17, 2025

(54) METHOD AND SYSTEM FOR JOINT DEMOSAICKING AND SPECTRAL SIGNATURE ESTIMATION

(71) Applicant: Hypervision Surgical Limited, London (GB)

(72) Inventors: Tom Vercauteren, London (GB); Michael Ebner, London (GB); Yijing Xie, London (GB); Eli Nabavi, London (GB)

(73) Assignee: Hypervision Surgical Limited, London (GB)

( * ) Notice: Subject to any disclaimer, the term of this patent is extended or adjusted under 35 U.S.C. 154(b) by 129 days.

(21) Appl. No.: 18/008,062

(22) PCT Filed: May 26, 2021

(86) PCT No.: PCT/GB2021/051280
§ 371 (c)(1),
(2) Date: Dec. 2, 2022

(87) PCT Pub. No.: WO2021/245374
PCT Pub. Date: Dec. 9, 2021

(65) Prior Publication Data
US 2023/0239583 A1    Jul. 27, 2023

(30) Foreign Application Priority Data

Jun. 3, 2020  (GB) ..................... 2008371
Feb. 19, 2021  (GB) ..................... 2102400

(51) Int. Cl.
*G01J 3/28*    (2006.01)
*A61B 1/00*    (2006.01)
(Continued)

(52) U.S. Cl.
CPC ...... *G01J 3/2823* (2013.01); *A61B 1/000094* (2022.02); *A61B 1/000096* (2022.02);
(Continued)

(58) Field of Classification Search
CPC .. G01J 3/2823; G01J 3/027; G01J 3/28; G01J 2003/1217; G01J 2003/283; G01J 3/0202;
(Continued)

(56) References Cited

U.S. PATENT DOCUMENTS

2010/0053346 A1* 3/2010 Mitsunaga ........... H04N 25/589
                                                     348/208.6
2015/0018645 A1   1/2015 Farkas et al.
(Continued)

FOREIGN PATENT DOCUMENTS

WO    2010/019515 A2    2/2010

OTHER PUBLICATIONS

Nov. 3, 2020—(GB) Search Report—GB2008371.3.
(Continued)

*Primary Examiner* — Albert H Cutler
(74) *Attorney, Agent, or Firm* — Banner & Witcoff, Ltd.

(57) ABSTRACT

Methods and systems for determining parameters of a desired target image from hyperspectral imagery obtained from a surgical procedure are described herein. Techniques may include capturing in real time hyperspectral snapshot mosaic images of a scene using a hyperspectral image sensor coupled to an optical scope, the snapshot mosaic images being of relatively low spatial and low spectral resolution; undertaking spatio-spectrally aware demosaicking of the snapshot mosaic images, the demosaicking comprising upsampling of the snapshot mosaic images and the application of a spectral calibration operator, to generate a virtual hypercube of the snapshot mosaic image data, the virtual hypercube comprising image data of relatively high spatial
(Continued)

resolution compared to the snapshot mosaic images; from the image data in the virtual hypercube, determining relatively high spatial resolution parameters of a desired target image; and outputting in real time the determined relatively high-resolution parameters as representative of the desired target image.

12 Claims, 19 Drawing Sheets

(51) Int. Cl.
*G06V 10/58* (2022.01)
*H04N 9/73* (2023.01)
*H04N 23/50* (2023.01)
*H04N 23/84* (2023.01)

(52) U.S. Cl.
CPC ............... *G06V 10/58* (2022.01); *H04N 9/73* (2013.01); *H04N 23/555* (2023.01); *H04N 23/843* (2023.01)

(58) Field of Classification Search
CPC ...... G01J 3/0218; G01J 3/0264; G01J 3/0291; A61B 1/000094; A61B 1/000096; A61B 5/0075; G06V 10/58; H04N 9/73; H04N 23/555; H04N 23/843; H04N 25/135
See application file for complete search history.

(56) References Cited

U.S. PATENT DOCUMENTS

| 2015/0141847 | A1* | 5/2015 | Sarvazyan ........... A61B 5/0036 600/478 |
| 2018/0184015 | A1* | 6/2018 | Richarte ................ H04N 23/60 |
| 2019/0096049 | A1 | 3/2019 | Kim et al. |
| 2019/0182441 | A1 | 6/2019 | Saleh et al. |
| 2020/0088579 | A1* | 3/2020 | Balas ................... G01J 3/2823 |

OTHER PUBLICATIONS

Dijkstra et al., "Hyperspectral demosaicking and crosstalk correction using deep learning", Springer, Jul. 26, 2018.
Nov. 25, 2021—(GB) Search Report—GB2102400.5.
Dombrowski et al., "Defeating Camouflage and Finding Explosives Through Spectral Matched-Filtering off Hyperspectral Imagery", SPIE, vol. 2933, 1997.
Oct. 4, 2021—(WO) International Search Report and Written Opinion—PCT/GB2021/051280.
Kanaev et al., "Imaging with multi-spectral mosaic-array cameras", Applied Optics, vol. 54, issue No. 31, Nov. 1, 2015.
Monno et al, "A Practical One-Shot Multispectral Imaging System Using a Single Image Sensor", IEEE Transactions on Image Processing, vol. 24, issue No. 10, Oct. 2015.
Tsagkatakis et al, "Graph and Rank Regularized Matrix Recovery for Snapshot Spectral Image Demosaicing", IEEE Transactions on Computational Imaging, vol. 5, No. 2, Jun. 1, 2019.
Waterhouse et al., "Specral band optimization for multispectral fluorescence imaging", SPIE, vol. 10057, Feb. 15, 2017.

* cited by examiner

Mosaic Array

Tiled Mosaic Array (b) Imec camera setup with adapter plate to connect with standard tripod systems (a) Photonfocus camera setup with heat sinks (c) Photonfocus snapshot of 4C patch with manually placed annotations for analysis (b) Spectrometer setup to acquire reference data (a) Checkerboard with 48 colour patches

METHOD AND SYSTEM FOR JOINT DEMOSAICKING AND SPECTRAL SIGNATURE ESTIMATION

CROSS-REFERENCE TO RELATED APPLICATIONS

This application is a U.S. National Stage application under 35 U.S.C. § 371 of International Application PCT/GB2021/051280, filed May 26, 2021, which claims the benefit of priority to United Kingdom Patent Applications GB 2008371.3, filed Jun. 3, 2020 and GB 2102400.5 filed Feb. 19, 2021. Benefit of the filing date of each of these prior applications are hereby claimed. Each of these prior applications are hereby incorporated by reference in their entirety.

TECHNICAL FIELD

Embodiments of the invention relate generally to image and video processing and in particular to a system and method for acquiring and processing hyperspectral images acquired in real time, and in some embodiments to images acquired in a medical context.

BACKGROUND TO THE INVENTION AND PRIOR ART

Many difficult intraoperative decisions with potentially life-changing consequences for the patient are still based on the surgeon's subjective visual assessment. This is partly because, even with the most advanced current surgical techniques, it may still not be possible to reliably identify critical structures during surgery. The need for more refined, less qualitative, intraoperative wide-field visualisation and characterisation of tissue during surgery has been evidenced across a variety of surgical specialties.

As a first example, in neuro-oncology, surgery is often the primary treatment, with the aim to remove as much abnormal tissue as safely possible (Gross Total Resection, GTR). The pursuit of GTR has to be balanced with the risk of postoperative morbidity associated with damaging sensitive areas that undertake vital functions such as critical nerves and blood vessels. During surgery, navigation solutions, such as those disclosed in U.S. Pat. No. 9,788,906 B2, can map preoperative information (e.g. MRI or CT) to the anatomy of the patient on the surgical table. However, navigation based on preoperative imaging does not account for intraoperative changes. Interventional imaging and sensing, such as surgical microscopy, fluorescence imaging, point-based Raman spectroscopy, ultrasound and intraoperative MRI, may be used by the surgeon either independently or as adjunct to navigation information to visualise the operated tissues. However, tissue differentiation based on existing intraoperative imaging remains challenging because of stringent operative constraints in the clinical environment (e.g. intraoperative MRI or CT), or imprecise tumour delineation (e.g. ultrasound or fluorescence imaging). In neuro-oncology surgery, fluorescence-guided surgery with 5-aminolevulinic acid (5-ALA) induced protoporphyrin IX (PpIX) has been increasingly used. Other fields including bladder cancer have also benefited from PpIX fluorescence guided surgery. However, the visualisation of malignant tissue boundaries is fuzzy due to accumulation of tumour marker also in healthy tissue; is non-quantitative due in part to the time-varying fluorescence effect and the confounding effect of tissue autofluorescence; is associated with side effects; and can only be used for specific tumour types as reviewed in Suero Molia et al., *Neurosurgical Review*, 2019. The wealth of prior art aiming at improving neurosurgical tissue differentiation is a clear indication that better intraoperative imaging is seen as an opportunity to improve patient outcomes in these difficult surgeries.

As a second example, Necrotising Enterocolitis (NEC) is a devastating neonatal disease often requiring surgical treatment with potential important side effects. NEC is characterised by ischaemic necrosis of intestinal mucosa, resulting in perforation, generalised peritonitis and, in severe cases, death of the newborn. Three in every thousand live births suffer from NEC with 85% of cases occurring in infants of very low birth weight (<1500 g) of whom 30% die despite state-of-the-art care as reviewed in Hull et al., *Journal of the American College of Surgeons*, 2014. Surgical management of NEC includes primary peritoneal drainage, exploratory confirmation surgery and/or laparotomy with bowel resection. A major challenge for surgeons performing NEC laparotomies is deciding how much bowel to resect, with long-term risk of leaving the baby with short bowel syndrome weighed against leaving poorly perfused bowel in situ, compromising the infant's chances of recovery. Currently, there is no standard of care image guidance technology for NEC laparotomy. Operative planning of the resection thus relies on the surgeon's judgment, dexterity and perceptual skills. If doubtful, crude incision of the tissue to assess bleeding may be used. It is thought that NEC mortality rates could be reduced by earlier diagnosis, better monitoring and improved surgical management.

As discussed in Shaper et al., *Journal of Biophotonics*, 2019, multispectral and hyperspectral imaging, hereafter jointly referred to as hyperspectral imaging (HSI) are emerging optical imaging techniques with the potential to transform the way surgery is performed. However, it remains unclear whether current systems are capable of delivering real-time, high-resolution tissue characterisation for surgical guidance. HSI is a safe, non-contact, non-ionising and non-invasive optical imaging modality with characteristics making it attractive for surgical use. By splitting light into multiple spectral bands far beyond what the naked eye can see, HSI carries refined information about tissue properties beyond conventional colour information that may be used for more objective tissue characterisation. In HSI, within a given time frame, the collected data spans a three-dimensional space composed of two spatial dimensions and one spectral dimension. Each such three-dimensional frame is commonly referred to as a hyperspectral image or hypercube. As illustrated in U.S. Pat. No. 6,937,885 B1, the concept of using HSI for medical applications has been known and explored for several decades. Classically, HSI has relied on scanning through space and/or spectrum to acquire complete hypercubes. Due to the time required for scanning purposes, these methods have been unable to provide a live display of hyperspectral images. Compact sensors capable of acquiring HSI data in real-time, referred to as snapshot HSI, have recently been developed. Such snapshot sensors acquire hyperspectral images at video rate, typically capable of achieving about 30 hyperspectral frames per seconds or even more, by sacrificing both spectral and spatial resolution. Instead of acquiring a dense hypercube—i.e. with fully sampled spectral information (z-direction) at each spatial pixel of a scene (x-y plane)—snapshot hyperspectral cameras acquire subsampled hyperspectral images in one shot typically using a tiled or mosaic pattern as detailed in Pichette et al., *Proc. of SPIE*, 2017.

Here, we define a hyperspectral imaging system to be real-time if it is capable of acquiring images at a video rate suitable for providing a live display of hyperspectral imaging information in the order of tens of frames per second.

As illustrated in Shape, et al., *Journal of Biophotonics*, 2019 and further detailed below in view of the prior art, while existing HSI systems can capture important information during surgery, they currently do not provide a means of providing wide-field and real-time information of high enough resolution to support surgical guidance.

Hyperspectral imaging for use in medical applications has been described with a number of different acquisition principles. The main ones have relied on sequential filtering of the light at the detector side. As an early example, U.S. Pat. No. 5,539,517 A proposed an interferometer-based method where a predetermined set of linear combinations of the spectral intensities is captured sequentially through scanning. Around the same time, U.S. Pat. No. 6,937,885 B1 proposed to acquire HSI data sequentially with the help of a tuneable filter such as a Liquid Crystal Tuneable Filters (LCTF) in combination with prior knowledge about expected tissue responses to acquire data according to a given diagnostic protocol. U.S. Pat. No. 8,320,996 B2 refined a programmable spectral separator, such as an LCTF, to acquire spectral bands one after the other, extract information related to a specific diagnostic protocol and proposed to project a summarising pseudo-colour image onto the imaged region of interest. In E.P. Pat. Application No. 2 851 662 A2, a slit-shaped aperture coupled with a dispersive element and mechanical scanning is used to acquire spectral imaging information in a sequential fashion. As these methods rely on sequential acquisition, they are not directly suitable for real-time wide-field imaging. Also, none of these works have presented a means of improving the resolution of the captured HSI.

In addition to filtering the light at the detector end, HSI for medical application has also been explored through the use of filtered excitation light. As a first example U.S. Pat. Application No. 2013/0245455 A1 proposed a HSI setup with a plurality of LED sources switched on in a particular order to acquire a plurality of spectral bands sequentially. In a similar approach, W.O. Pat. Application No. 2015/135058 A1 presented an HSI system which requires optical communication between a remote light source and a spectral filtering device to scan through a set of illumination filters. As with their detection filtering counterparts, these systems are not suitable for real-time imaging and no solution for HSI resolution improvement is provided.

Still in the medical domain, HSI data sources have been integrated in more complex setups, some of which looking into providing pathology-related discriminative information. U.S. Pat. Application No. 2016/0278678 A1 relies on projecting spatially modulated light for depth-resolved fluorescence imaging combined with hyperspectral imaging. U.S. Pat. No. 10,292,771 B2 disclosed a surgical imaging system potentially including an HSI device and exploiting a specific surgical port with a treatment to decrease the reflectance of the port. In U.S. Pat. No. 9,788,906 B2, hyperspectral imaging is used as a potential source of information to detect the phases of a medical procedure and correspondingly configuring an imaging device. HSI-derived tissue classification is disclosed in E.P. Pat. Application No. 3545491 A1 where clustering is used to assign the same classification to all the pixels belonging to the same cluster. Tissue classification based on HSI data is also presented in W.O. Pat. Application No. 2018/059659 A1. Although of potential interest for use during surgery, none of these imaging systems propose a means of acquiring real-time HSI or a means to improving the resolution of HSI images, and nor do they propose a means of generating high-resolution tissue characterisation of classification maps.

Whilst HSI has been investigated for the assessment of various clinical conditions such as peripheral vascular disease [11], retinal eye disease [12], hemorrhagic shock [13], healing in foot ulcers of diabetic patients [14] and cancer detection [15], its in vivo surgical use has been restricted to a few clinical research cases only [5]. For example, while the HELICoiD research system [10] demonstrated promising clinical research results for in vivo brain tumour detection [16], its size is prohibitive for clinical adoption during surgery. Other systems presented for the intraoperative assessment of tissue perfusion and oxygenation—including breast [17], oral cancer [7], renal [18], epilepsy [19], neurovascular [8] and gastrointestinal surgery [20, 21]—further demonstrate the potential of intraoperative HSI (iHSI). Yet, these are prone to produce motion artefacts due to insufficient imaging speed for a dynamic scene during surgery. More recently, two intraoperative systems based on pushbroom HSI cameras were presented that allow for integration into the surgical workflow: In [22], a pushbroom HSI system [23] was attached to a surgical microscope to capture in vivo neurosurgery data; and in [24], a laparoscopic HSI camera was presented and tested during esophagus surgery. While these systems show potential to support the surgical workflow, their restricted imaging speed is likely to remain an inhibitor for adoption during surgery.

For increased real-time imaging speed, as also mentioned above in the section related to acquiring images, recently developed snapshot HSI camera systems have been used to assess brain perfusion in neurosurgery [25] and to perform preclinical skin perfusion analysis [26]. However, while snapshot HSI sensors permit real-time HSI capture with video-rate imaging, spatial resolution is limited and needs to be accounted for in a postprocessing step called demosaicking [27, 28]. Moreover, previously presented snapshot iHSI works did not methodologically map out and address the critical design considerations to ensure a seamless integration into the surgical workflow.

While various HSI systems have been tested in a surgical environment to investigate the potential of iHSI, to the best of our knowledge, no HSI system has been presented allowing for strict clinical requirements including a means of maintaining sterility and ensuring seamless integration into the surgical workflow that can provide real-time information for intraoperative surgical guidance.

Outside of the medical field, sensors able to acquire HSI data in real-time have recently been proposed. In E.P. Pat. Application No. 3348974 A1, a hyperspectral mosaic sensor is presented in which spectral filters are interleaved at the pixel level to generate spatially and spectrally sparse but real-time HSI data. A number of aberrations are expected in such sensors and Pichette et al., *Proc. of SPIE*, 2017 presented a calibration approach able to compensate for some of the observed spectral distortions but no method was presented there to increase the spatial resolution. In Dijkstra et al., *Machine Vision and Applications*, 2019, a learning-based approach for snapshot HSI acquired with a mosaic sensor is presented. In particular, a hypercube reconstruction approach is presented. This approach focuses only on demosaicking/crosstalk correction for hypercube reconstruction. However, they do not disclose extracting parameters of a desired target image from hyperspectral imagery. Although the effect of spectral cross-talk and the sparse nature of the sensor are discussed in this work, the combined effect of various distortions is not modelled or captured directly. Simplifying assumptions are used to decouple crosstalk-correction and upscaling. Alternative means of capturing snapshot HSI data have been proposed such as coded aperture snapshot spectral imaging (CASSI) presented in Wagadarikar et al., *Applied Optics*, 2008. These imaging systems typically include a number of optical elements such as dispersive optics, coded apertures, and several lenses often resulting in an impractical form factor for use in surgery. Similar to mosaic sensors, CASSI systems result in difficult trade-offs between temporal, spectral, and spatial resolution but also lead to complex and computationally costly reconstruction techniques. U.S. Pat. Application No. 2019/0096049 A1 proposed to combine learning-based techniques with optimisation techniques to reconstruct CASSI-based HSI data. Even though the computational complexity was reduced, and although the system is able to capture raw data in real-time, the system does not disclose a means of performing real-time reconstruction. Even though sensors such as mosaic sensor and CASSI may find a use in surgery, it remains to be shown how these can be integrated in a real-time system able to display high-resolution HSI-derived images and concurrently provide maps such as tissue characterisation or discriminative images of tissue classification for surgical support.

Prior art shows that the problem of intraoperative tissue characterisation arises in many surgical fields and that it has been addressed with different methods. Hyperspectral imaging has notably shown great potential in this area. However, to the best of our knowledge, there is no disclosure of a method that can provide wide-field and high-resolution tissue-related information derived in real-time from hyperspectral imaging during surgery. Therefore, a need exists for a system and method that would allow for real-time resolution improvement and associated tissue characterisation of hyperspectral imaging.

SUMMARY OF INVENTION

Embodiments of the invention provide a method and system that allows parameters of a desired target image to be determined from hyperspectral imagery of scene. The parameters may be representative of various aspects of the scene being imaged, particularly representative of physical properties of the scene. For example, in some medical imaging contexts, the property being imaged may be blood perfusion or oxygenation saturation level information per pixel. In one embodiment the parameters are obtained by collecting lower spectral and spatial resolution hyperspectral imagery, and then building a virtual hypercube of the information having a higher spatial resolution using a spatiospectral-aware demosaicking process, the virtual hypercube then being used for estimation of the desired parameters at the higher spatial resolution. Alternatively, in another embodiment, instead of building the virtual hypercube and then performing the estimation, a joint demosaicking and parameter estimation operation is performed to obtain the parameters in high spatial resolution directly from lower spectral and spatial resolution hyperspectral imagery. Various white level and spectral calibration operations may also be performed to improve the results obtained.

With particular reference to development of a system for hyperspectral imaging, our contributions are four-fold: (i) contrary to previous work [29], we systematically capture a set of design requirements, including functional and technical requirements, critical for an iHSI system to provide real-time wide-field HSI information for seamless surgical guidance in a highly constrained operating room (OR); (ii) we present and evaluate a set of iHSI embodiments against these requirements by considering two state-of-the-art industrial HSI camera systems based on linescan and snapshot imaging technology; (iii) we perform ex vivo animal tissue experiments in a controlled environment with exemplar iHSI embodiments to investigate tissue properties using both camera systems; and (iv) we report the use of a real-time iHSI embodiment (FIG. 5) during an ethically-approved in-patient clinical feasibility case study as part of a spinal fusion surgery therefore successfully validating our assumptions that our invention can be seamlessly integrated into the OR without interrupting the surgical workflow.

In view of the above, from a first aspect there is provided a method of determining parameters of a desired target image from hyperspectral imagery, comprising: capturing hyperspectral snapshot mosaic images of a scene using a hyperspectral image sensor, the snapshot mosaic images being of relatively low spatial and low spectral resolution; undertaking demosaicking of the snapshot mosaic images to generate a virtual hypercube of the snapshot mosaic image data, the virtual hypercube comprising image data of relatively high spatial resolution compared to the snapshot mosaic images; from the image data in the virtual hypercube, determining relatively high spatial resolution parameters of a desired target image; and outputting the determined relatively high-resolution parameters as representative of the desired target image.

In one example the demosaicking is spatiospectrally aware. For example, the demosaicking may comprise image resampling, such as linear or cubic resampling, of the snapshot mosaic images followed by the application of a spectral calibration matrix. Moreover, in another example the demosaicking may comprise machine learning.

In addition or alternatively, the demosaicking may be temporally consistent between two or more consecutive frames based on motion compensation in between frames.

A further example further comprises, prior to capturing the hyperspectral snapshot mosaic images, undertaking a white balancing operation on the hyperspectral image sensor. In one example the white balancing operation may comprise separately acquiring reference images, including dark and white reference mosaic images $w_{d;\tau_d}$ and $w_{w;\tau_w}$ at integration times $\tau_d$ and $\tau_w$, respectively, and deploying a linear model where in addition to the acquired mosaic image $w_\tau$ of an object with integration time $\tau$, a white reference mosaic image $w_{w;\tau_w}$ of a reflectance tile with integration time $\tau_w$, and dark reference mosaic images $w_{d;\tau}$ and $w_{d;\tau_w}$ are acquired with integration times $\tau$ and $\tau_w$, with a closed shutter, and the white balancing operation yields a reflectance mosaic image given by $$r := \frac{w_\tau - w_{d;\tau}}{w_{w;\tau_w} - w_{d;\tau_w}} \frac{\tau_w}{\tau} \in W.$$

In a further example, prior to capturing the hyperspectral snapshot mosaic images, a spatiospectral calibration operation is undertaken on the hyperspectral image sensor. During the calibration operation a real spectral filter response operator $B_F: \mathbb{R}^{n_A} \to \mathbb{R}^{m_1 m_2}$ and a spatial cross-talk operator $T: W \to W$ are estimated in a controlled setup to account for parasitical effects during image acquisition.

In addition, a further example may further comprise measuring a characteristic of the hyperspectral image sensor to obtain a measured system filter response operator $A_F^{meas}: U \to W$ by acquiring snapshot mosaic image data using collimated light and sweeping through all $n_A$ wavelengths in conjunction with an imaging target with known, typically spatially-constant, spectral signature.

In one example, the determining of the relatively high spatial parameters further comprises analysing pixel-level hyperspectral information for its composition of unique end-members characterised by specific spectral signatures.

In one example, the determining of the relatively high spatial parameters further comprises estimation of tissue properties per spatial location (typically pixels) from reflectance information of hyperspectral imaging, such as pixel-level tissue absorption information.

Another example of the present disclosure provides a method of determining parameters of a desired target image from hyperspectral imagery, comprising: capturing hyperspectral snapshot mosaic images of a scene using a hyperspectral image sensor, the snapshot mosaic images being of relatively low spatial and low spectral resolution; undertaking a joint demosaicking and parameter estimation from the snapshot mosaic images to determine relatively high spatial resolution parameters of a desired target image; and outputting the determined relatively high-resolution parameters as representative of the desired target image. Within this additional example all of the white balancing and calibration operations noted above may also be employed A further aspect of the present disclosure provides a system for hyperspectral imaging of a target region, comprising: a light source for illumination of the target region; a hyperspectral image sensor configured to capture one or more hyperspectral images of the target region; an optical scope coupled to the hyperspectral image sensor such that, during use, an image of the target region, produced by the optical scope, is acquired by the hyperspectral image sensor.

In one example, a system according to the present disclosure is a system for hyperspectral imaging of a target region, comprising: a light source for illumination of the target region; and at least one hyperspectral image sensor configured to capture a hyperspectral image of the target region, wherein the system is configured to acquire a plurality of hyperspectral sub-images of the target region on the at least one image sensor.

In one example, a system according to the present disclosure is a system for hyperspectral imaging of a target region, comprising: a light source for illumination of the target region; and a hyperspectral image sensor configured to capture a hyperspectral image of the target region, wherein the system is arranged to control the switching of the light source at a predetermined frequency.

In a further example, a system according to the present disclosure is a system for hyperspectral imaging of a target region, comprising: a light source for illumination of the target region; and a hyperspectral image sensor configured to capture a hyperspectral image of the target region, wherein the system comprises a means for heat dissipation coupled to the hyperspectral image sensor.

The system in any of the above-mentioned examples may be further configured to determine parameters of the target region from hyperspectral imagery, the system further comprising: a processor; and a computer readable storage medium storing computer readable instructions that when executed by the processor cause the processor to control the system to perform the method as described earlier in this section.

In addition, another example provides a computer readable storage medium storing a computer program that when executed causes a hyperspectral imaging system, according to any of the above-specified examples, to perform the method of any of the above examples as described earlier in this section. Further features and aspects of the invention will be apparent from the appended claims.

BRIEF DESCRIPTION OF THE DRAWINGS

Further features and advantages of the present invention will become apparent from the following description of an embodiment thereof, presented by way of example only, and by reference to the drawings, wherein like reference numerals refer to like parts, and wherein.

OVERVIEW OF EMBODIMENTS

According to one aspect, embodiments described herein relate to a computer-implemented method and a computer system for obtaining hyperspectral images from lower resolution mosaic image data acquired in real time, in order to determine image property information representative of some physical property of the sample being imaged. The method may comprise:

the acquisition of hyperspectral imaging data with a medical device suitable for use in a sterile environment the application of data-driven computational models to deliver hyperspectral information at a strictly higher resolution than any spectral band of the original data An imaging system for data acquisition for use with the method and system may consist of one or more hyperspectral imaging (HSI) cameras and a light stimulus provided by one or more light sources. Its application can be combined with a scope, such as an exoscope or endoscope, to be provided as part of the optical path of the imaging system.

The imaging system may be hand-held, fixed to a surgical table for example by means of a mechanical arm or combined with a robotic actuation mechanism.

Optical filters may be placed in the optical path anywhere in between the origin of the travelling light and its receiving end such as a camera sensor.

Hyperspectral images may be acquired with an imaging device that captures sparse hyperspectral information such as by assigning each spatial location the spectral information of strictly fewer spectral bands than the total number of spectral bands the imaging system is capable of measuring. An example of such a prior art imaging system is shown in U.S. Pat. No. 9,857,222 B, and that describes using a mosaic of filters for passing different bands of the optical spectrum, and a sensor array arranged to detect pixels of the image at the different bands passed by the filters, wherein for each of the pixels, the sensor array has a cluster of sensor elements for detecting the different bands, and the mosaic has a corresponding cluster of filters of different bands, integrated on the sensor element so that the image can be detected simultaneously at the different bands.

Figure 1:
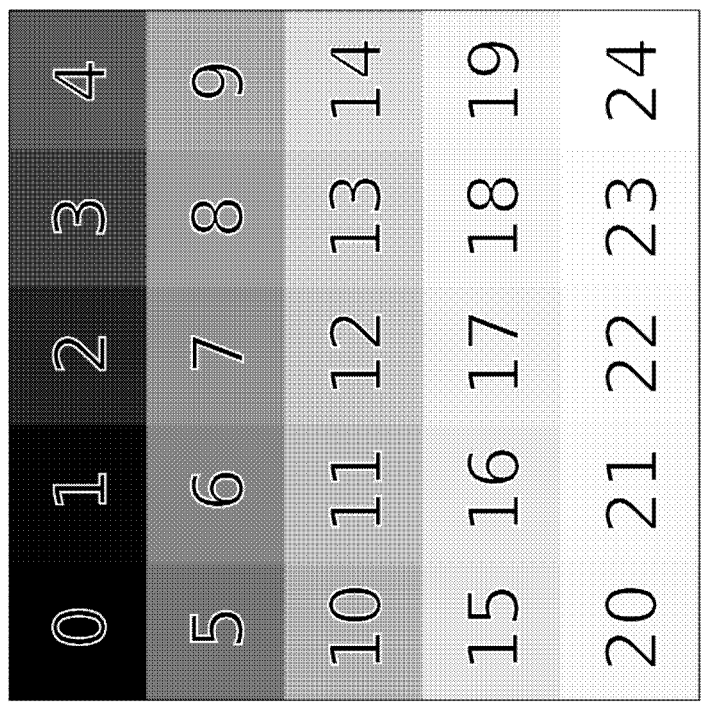
FIG. 1 is a display illustrating a typical arrangement of filters in a mosaic sensor.
Figure 2:
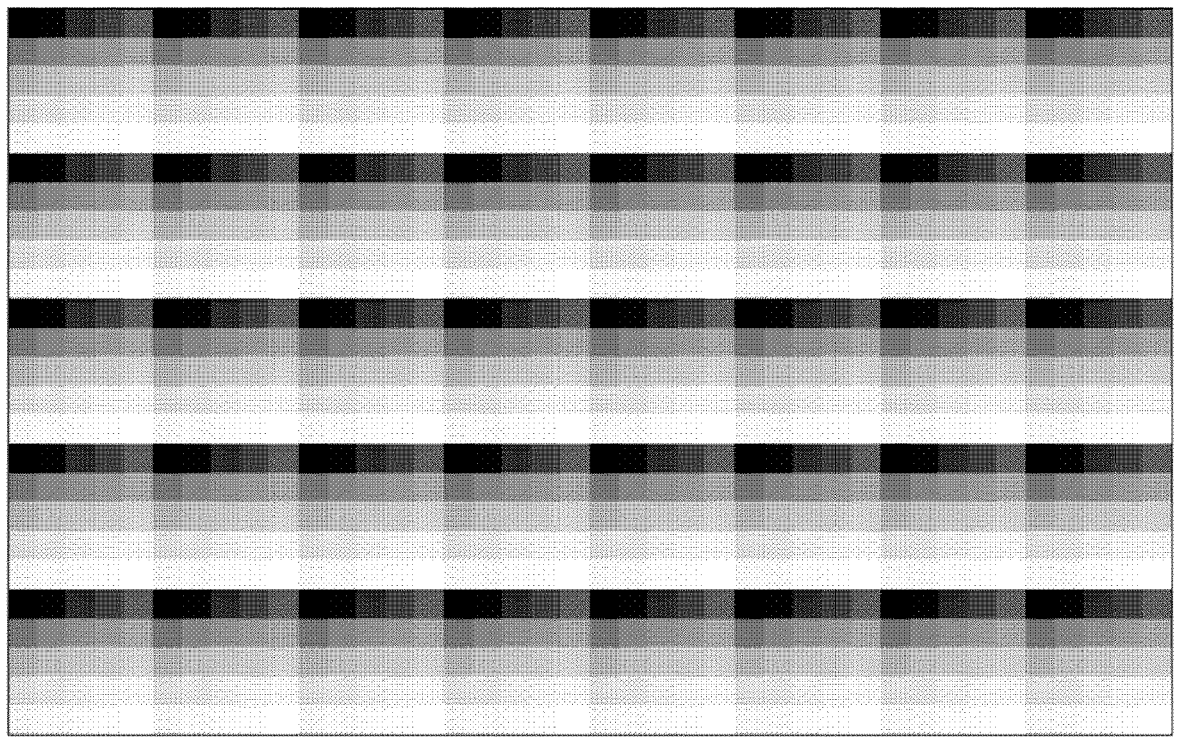
FIG. 2 is a display that schematically represents a mosaic sensor array that comprises the active sensor area of a snapshot mosaic imaging system.
Figure 2:
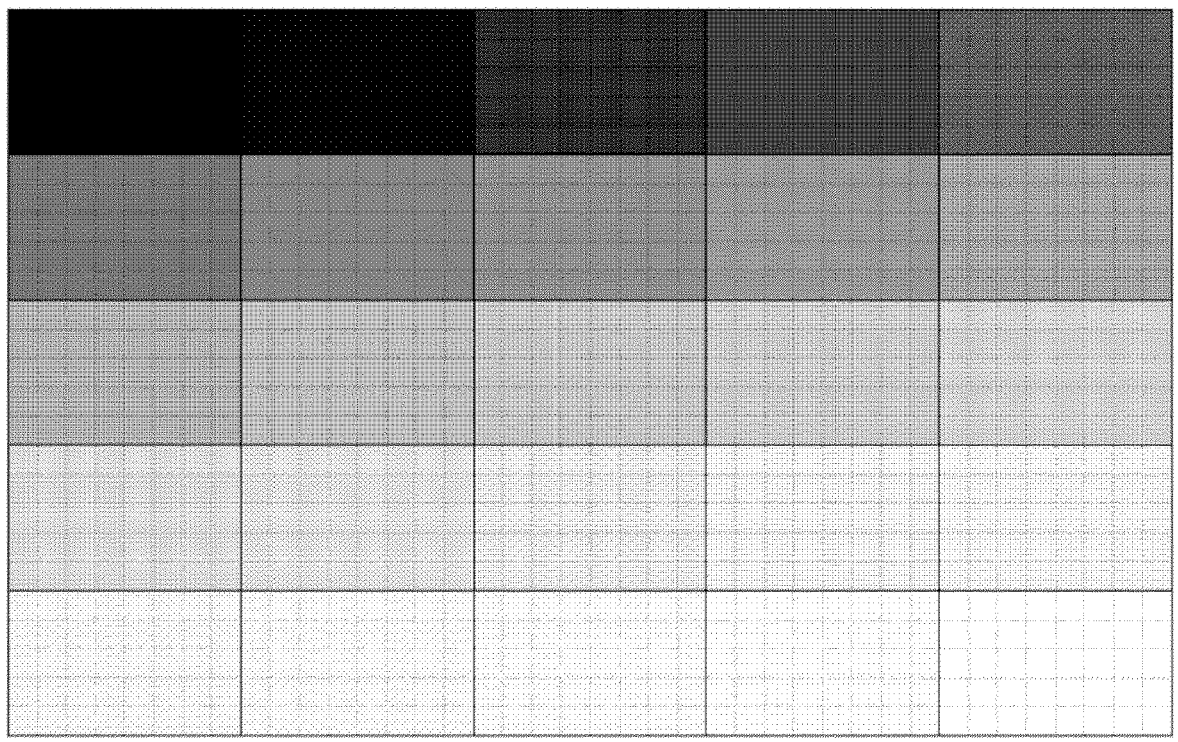

An example imaging system may include a sensor array of individual 5×5 mosaic sensor as shown in FIG. 1. The active sensor area is obtained by creating an array of such individual mosaic sensors (see FIG. 2). Each 5×5 mosaic sensor integrates 25 optical filters that are sensitive to different spectral bands. This leads to a sparse sampling of hyperspectral information across the active sensor area where each spectral band information is acquired only once per 5×5 region and spatially shifted with respect to other bands. An image acquired by such a sensor array arrangement shall be called a 'mosaic' or 'snapshot mosaic' image.

Figure 3:
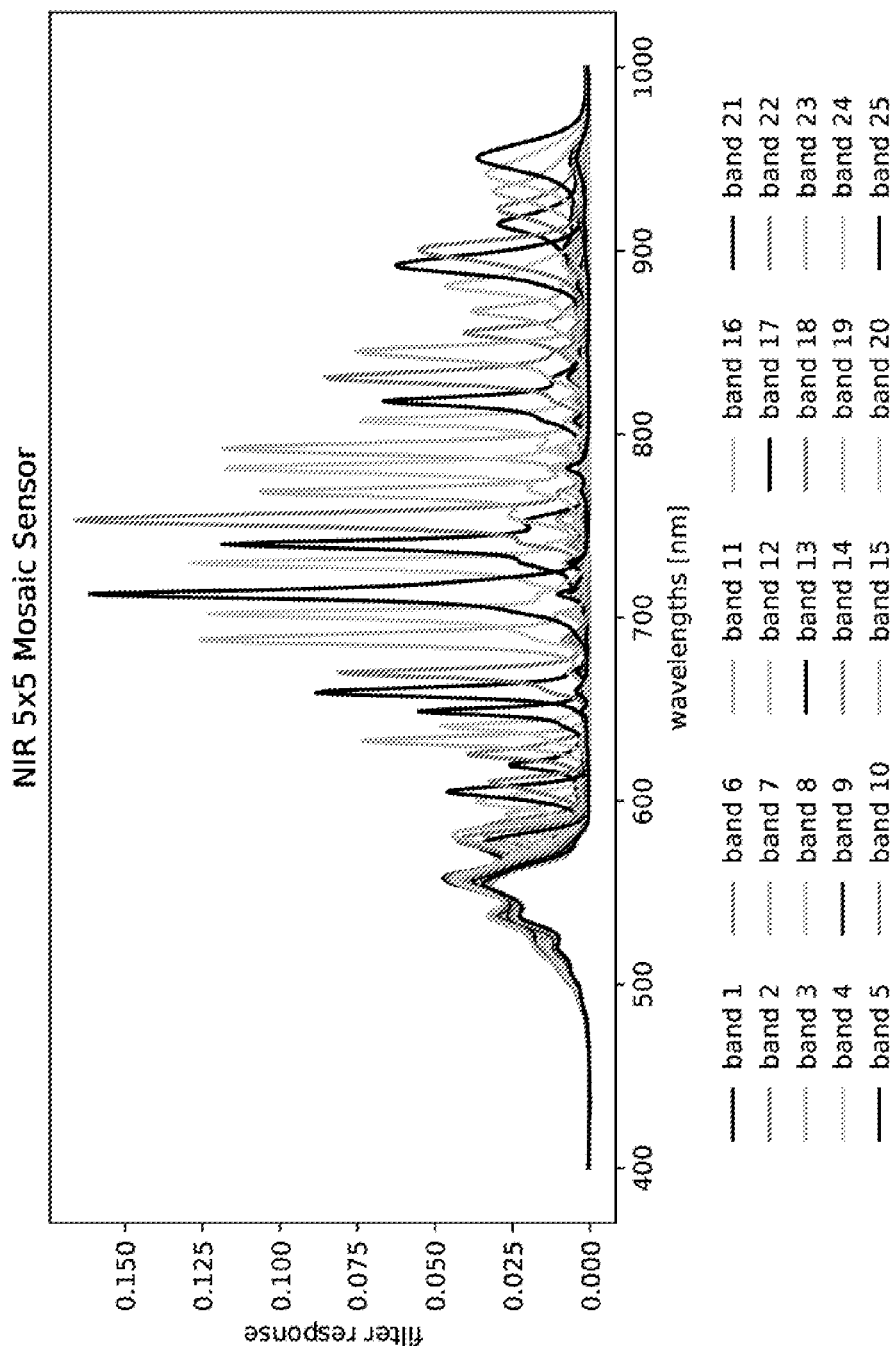
FIG. 3 is a graph showing example responses of a near-infrared 5×5 mosaic sensor.

Due to imperfections and physical design constraints of the hyperspectral camera sensor in practice, parasitic effects may lead to multimodal sensitivity response curves of the optical filters. Examples of such effects affecting the imaging include interference of higher-order spectral harmonics, out-of-band leakage and cross-talk between neighbouring pixels on the camera sensor. Example response curves for a near-infrared (NIR) 5×5 mosaic sensor are shown in FIG. 3. As will be made clear, additional filters may be used to suppress or emphasise spectral parts of these responses. A naive hypercube reconstruction from a snapshot mosaic image obtained by stacking images of band-associated pixels onto each other leads to a spatially and spectrally distorted hypercube representation that is low-resolution in both spatial and spectral dimensions. Therefore, snapshot hyperspectral imaging is characterized by a high temporal resolution of hyperspectral images that are affected by multimodal spectral band contamination and are low-resolution in both spatial and spectral dimensions.

Herein, we disclose methods suitable to obtain hyperspectral imaging information in high temporal and spatial resolution from snapshot imaging that provides wide-field and high-resolution tissue-related information during surgery in real-time.

White balancing and spatiospectral calibration of acquired hyperspectral snapshot mosaic images may be done as a preprocessing step with data acquired either in factory or with data acquired by the user. In some examples this may be achieved by using a single image of a static object, such as a reflectance board, or a sequence of images of either a static or moving object, acquired in or outside of the operating theatre. In some other examples, this may be done by processing specular reflections as observed in the acquired image data. Further examples for image calibration may relate to image processing due to a deliberate change of the imaging device settings, such as changing the effects of filter adjustments.

The reconstruction of a higher-resolution hyperspectral image data from the original, low-resolution snapshot mosaic using image processing methods shall be referred to as 'demosaicking' or 'upsampling'. Demosaicking may be performed by spatiospectrally upsampling the acquired snapshot mosaic data to obtain a hypercube with a fixed, potentially arbitrary, number of spectral band information for all acquired image pixel locations. In some embodiments, such demosaicking may also be performed to achieve spatiospectral upsampling onto a high-resolution grid other than the original image pixel locations. Besides conventional demosaicking approaches that achieve spatial upsampling due to, e.g., resampling, we present spatiospectral-aware upsampling/demosaicking methods that account for both spatial cross-talk and spectral parasitical effects specifically important in snapshot imaging systems. Such a reconstruction shall be referred to as a 'virtual hypercube'. Simple examples of demosaicking may include image resampling performed independently for each spectral band. In other examples, this may include methods based on inverse problem formulations. Other examples may also include the use of data-driven, supervised, semi-supervised or unsupervised/self-supervised machine learning approaches. These examples may also include computational methods for reconstructions that are designed for irregular grids. Increased quality or robustness during demosaicking may be obtained by processing a video stream of image data. Similar approaches may be used to increase temporal resolution for data visualisation.

Figure 4:
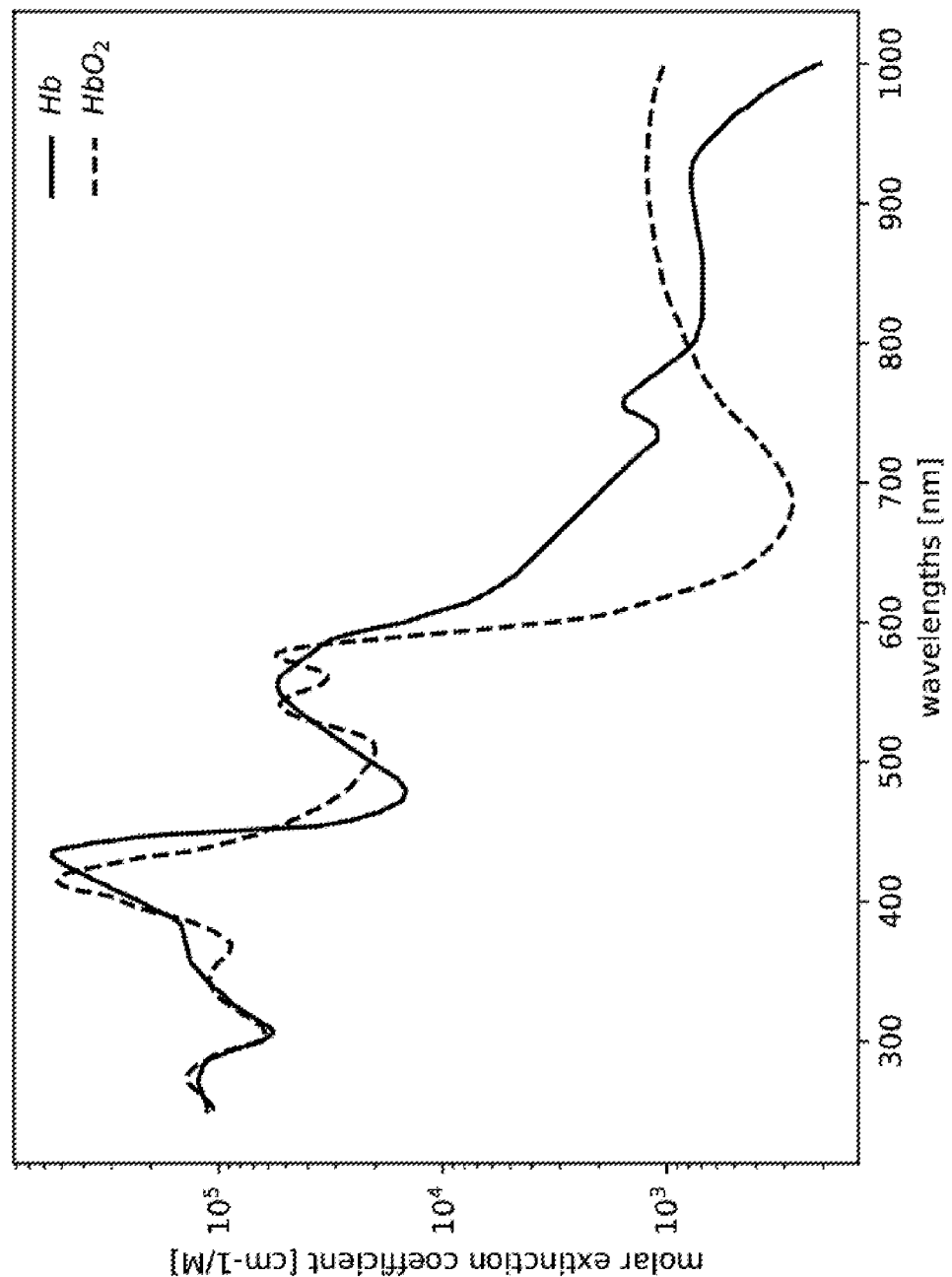
FIG. 4 is a display illustrating the molar extinction coefficient for oxy-($HbO_2$) and deoxy-haemoglobin (Hb).

Computational models may be used for parameter estimation from a virtual hypercube representation. Examples may include the estimation of tissue properties per spatial location (typically pixels) from reflectance information of hyperspectral imaging, such as pixel-level tissue absorption information. More generally, the obtained pixel-level hyperspectral information may be analysed for its composition of unique end-members characterised by specific spectral signatures. Spectral unmixing algorithms are presented that estimate the relative abundance of end-members mixed in pixel spectra to derive tissue properties relevant for surgical guidance. Relevant examples of end-members include oxy- and deoxy-haemoglobin (FIG. 4). Examples of relevant end-member-derived tissue properties include blood perfusion and oxygenation level saturation level information per pixel.

Other examples of unmixing may include the estimation of fluorescence and autofluorescence which may also be used for quantitative fluorescence.

In another aspect, virtual hypercube representation may serve to estimate a pseudo red-green-blue (RGB) image or any other image of reduced dimensionality to visualize hyperspectral imaging data.

According to another aspect, virtual hypercubes may also be used to classify pixels according to tissue type, including the types of benignity and malignancy. Virtual hypercubes may also be used for semantic segmentation beyond tissue types. This may include the classification of any pixel associated with non-human tissue such as surgical tools. Obtained segmentations may be used for increased robustness of tissue parameter estimation or to correct potential image artefacts such as specular reflections.

In all examples described in here, virtual hypercube estimation and parameter extraction may be performed at two independent steps or may be performed jointly. Computational models may use algorithms which allow for joint demosaicking and parameter estimation. Such approaches may be based on inverse-problems formulations or on supervised or unsupervised machine learning approaches.

All computer-assisted parameter estimations may be associated with uncertainty estimates.

Figure 5:
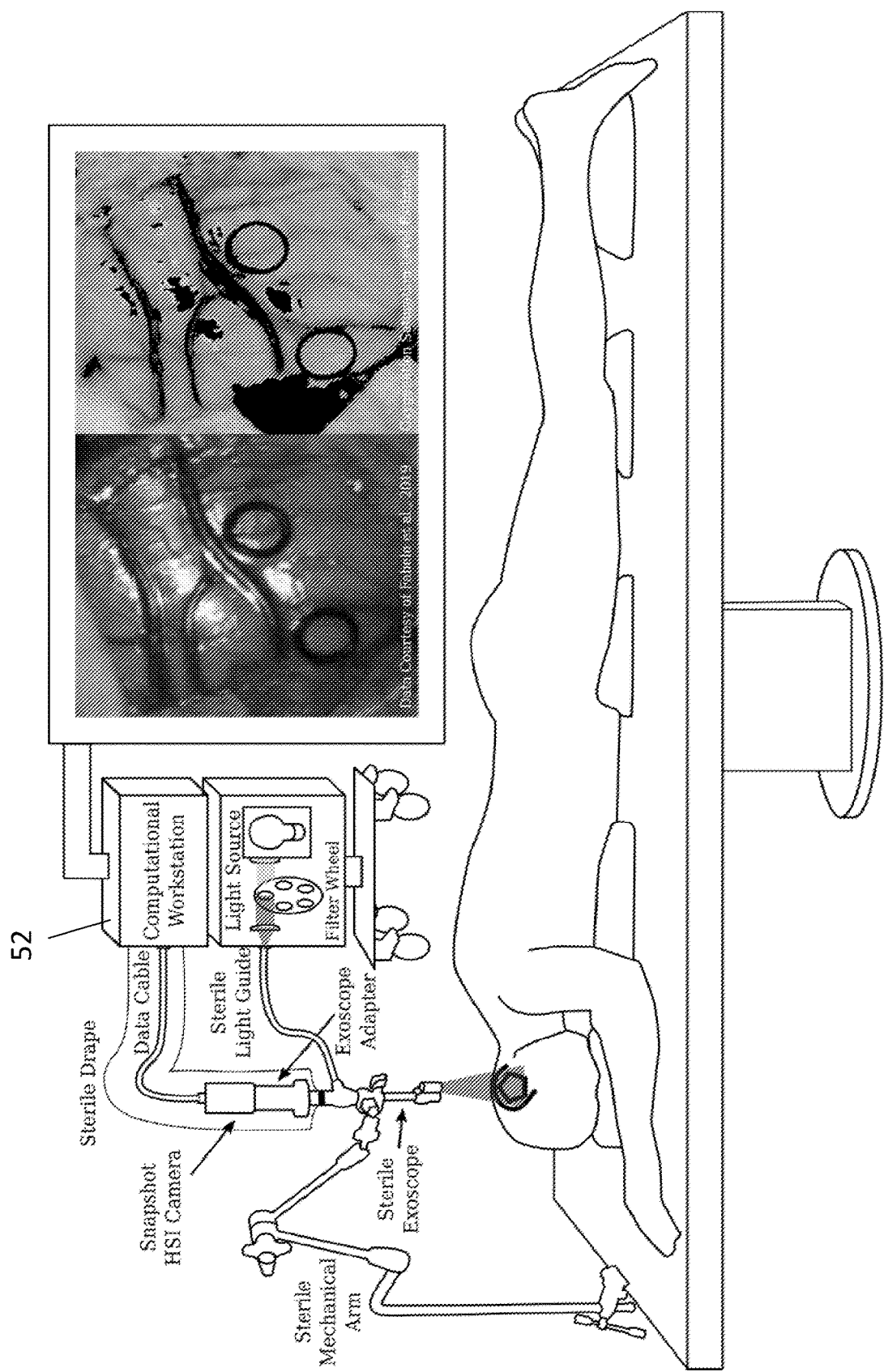
FIG. 5 is a diagram describing an example of a sterile imaging system that may be used for real-time hyperspectral imaging.

The present disclosure relates to an image processing system and method that may allow video processing of high-resolution hypercube data to be performed online from a video stream of sparse, low-resolution mosaic data acquired in real time by a medical device suitable for use in a sterile environment Description of the System FIG. 5 presents an overview of an example sterile imaging system that may be used for real-time hyperspectral imaging. A real-time hyperspectral imaging camera, such as a snapshot hyperspectral camera, is mounted on a sterile optical scope, such as a sterile exoscope, via an appropriate adapter. This adapter may also allow for zooming and focusing of the optical system and may comprise additional features such as a mechanical shutter, a beam splitter or a filter adapter. In some embodiments, the use of several camera sensors combined with light splitting mechanisms may be advantageous to cover the range of wavelengths of interest. For ease of presentation, such configuration may continue to be referred to as a hyperspectral imaging camera. The sterile optical scope is connected to a light source, such as a broadband Xenon or LED light source that can provide light for spectral wavelengths appropriate for the hyperspectral imaging camera or for exciting fluorophores of interest via a light guide which may be sterile or draped. It should be clear that light sources may in some embodiments also be mounted together with the camera, thereby potentially foregoing the need for a light guide. Optical filters may be placed in the optical path anywhere in between the origin of the travelling light and its receiving end such as the camera sensor. Such optical filters may be inserted using a variety of means such as a filter wheel within the light source that may hold multiple optical filters or may be embedded in the adapter or endoscope. In some embodiments, optical filters may be used to eliminate undesired out-of-band responses, such as parts of the visible light for an NIR sensor (FIG. 3). The hyperspectral imaging camera is connected to a computational workstation via a data link such as a cable or a wireless communication. Advantageously, electrical power may be provided to the camera sensor and other powered elements mounted with the camera (e.g. tuneable lens or filter) through the same cable as the data link as would be with Power over Ethernet (Poe) connection. The workstation processes acquired hyperspectral imaging information and derived information may be displayed to a user via a display monitor. In some embodiments, the workstation may be embedded in the camera sensor unit or in the display monitor. Visualized information may include the acquired hyperspectral imaging data, or derived information thereof via computational methods described below, such as RGB image or tissue property information. Overlay of different types of information may be used to provide more context to the user. In one example, tissue property information in an area where estimation is done with high confidence can be overlaid on a pseudo-RGB rendering of the captured scene. Sterility of the imaging system may be ensured by a combination of draping or sterilising of the system components and procedural step to ensure connection between sterile and non-sterile components do not compromise the sterility of the sterile operators and field. One advantageous embodiment can be to use a sterile drape for the camera and the data cable which is sealed on a sterile optical scope connected to a sterile light guide. The sterile imaging system may be hand-held by the user or fixed to a surgical table that allows controlled mobilisation or immobilisation of the imaging system depending on the user's requirement during surgery. Controlled mobilisation and immobilisation of the sterile imaging system may be achieved using a sterile or draped mechanical arm or robotic actuation mechanism. In other embodiments, the hyperspectral imaging system may be embedded in a surgical microscope.

More generally, we will now present the key design requirements of HSI for intraoperative surgical guidance suitable for open surgery. By following these criteria, the iHSI invention, embodied and illustrated in FIG. 5, is introduced and described in more detail.

Intraoperative HSI System Design Requirements

A first design assumption is that the intraoperative application of an HSI camera system is facilitated by developing a standalone light-weight device independent of or complementary with an operating microscope typically used for neurosurgery. In particular, by ensuring compatibility with surgical telescopes, such as an exoscope or endoscope, as well as surgical microscopes, a modular and flexible system design is achieved and is suitable for both open or endoscopic surgery across surgical specialties. Following this assumption, Table 1 and Table 2 provides an overview of design requirements considered to embody a hyperspectral imaging system for intraoperative surgical guidance including minimum and target requirements. These are divided into (i) functional requirements, i.e. requirements stemming from the clinical environment in the OR during surgery (Table 1), and (ii) technical requirements, i.e. specifications for a HSI system to achieve high-fidelity imaging data to satisfy the listed functional requirements for the purpose of real-time surgical guidance (Table 2). When objective requirements are not readily provided, best estimates are given based on our experience as outlined below.

As part of surgical requirements, ensuring sterility of the iHSI system is beneficial so that safe handling by the surgical team is possible (F1), it is beneficial to adhere to standard technical safety specifications (F2), light an illumination requirements should advantageously not impede surgical workflow (F3), and the device should advantageously be easy to maintain and clean in compliance with standard surgical practice (F4). It should advantageously be securely mounted during the procedure but the handheld device should advantageously be easily maneuverable, allowing for controlled mobilisation and immobilisation of the imaging system by a single operator without the need for an assistant (F5). The spatial resolution and spectral information captured within the surgical image should advantageously be compatible with the surgical action (F6), i.e. the provision of wide-field information covering the minimal region that provides sufficient context for surgical decision making. In addition, it should advantageously facilitate the ability of broader tissue surveillance relevant to the surgery. The device should advantageously be capable of providing critical functional or semantic tissue information and should be capable of providing detailed information on multiple features for comprehensive patient monitoring in order to increase surgical precision and patient safety during the procedure (F7). In the case of neuro-oncology surgery, this might be the demarcation of tissue boundaries to clearly demonstrate tumour tissue and its relation to critical brain structures such as nerves, blood vessels or normal brain. Furthermore, image resolution should advantageously be sufficiently detailed to facilitate spatial differentiation between tissue types within the surgical field of view F8). Imaging should advantageously be displayed at video-rate to facilitate instant surgeon feedback and seamless workflow integration with higher video-rates allowing for a smoother experience (F9). Accurate visualisation of extracted information is advantageous for surgical guidance whereby a better user experience can be achieved using intuitive display systems F10.

To ensure surgical safety and sterility, system maintenance should advantageously be straightforward and it should advantageously be possible to clean the system's components effectively using a standard antimicrobial surface wipe (T1). The minimum advantageous requirements of HSI camera dimensions and weight are based on the estimates in [29] obtained through a prototyping-testing design thinking methodology [31], i.e. a camera smaller than 10×10×12 cm3 (T2) and lighter than 1.0 kg (T3). For a system with dimensions smaller than 6×6×8 cm3 standard drapes for covering the camera can be used to ensure sterility. Additionally, all camera edges should advantageously be smooth to prevent tearing of sterile drapes and injuring of staff members (T4). A maximum camera temperature of 40° C. advantageously ensures technical safety for device handling in addition to reduced dark currents for maintaining appropriate signal-to-noise ratios (SNRs) during image acquisition (T5). The number of cables for powering of and data connection with the camera should advantageously be kept at a minimum (T6). To enable adequate iHSI, a suitable light source should advantageously be available to provide sufficient energy across the active spectral range of the HSI camera (T7), but technical safety and light safety considerations should advantageously be adhered to so that no injury is caused to the patient due to light exposure (T8). This includes advantageously adhering to the maximal permissible exposure (MPE) in particular with ionizing ultraviolet (UV) wavelengths below 400 nm [32]. Light source setting adjustments should advantageously be possible to allow optimal illuminant conditions for acquiring HSI information during surgery (F3 and T10). Besides optimal light intensity settings depending on the surgical scene, this may advantageously include adjustment of optical filters to acquire high-fidelity HSI signal measurements depending on the imaging requirements of the HSI camera. Advantageously, these settings can be adjusted by automatically accounting for dynamic changes in the OR such as illumination. A static mounting system is the minimum advantageous requirement to allow adequate intraoperative device handling (T9). Camera settings can advantageously be adjusted depending on the surgical context to acquire high-fidelity HSI information (T10) including by achieving an adjustable system mount (T9), enabling automated adjustments to the camera settings (T10). By meeting the advantageous target requirements for camera dimension and weight (T2, T3), further improvements in device handling can be achieved.

High-fidelity tissue information may benefit from the respective target tissue being within the imaging field of view and kept in focus during HSI acquisition. During surgery this may require re-focusing which can either be achieved using manual or autofocus arrangements (T11). A fixed working distance (WD) between 200 mm and 300 mm (T12) with a fixed field of view (FOV) between 40 mm and 60 mm (T13) and a depth of field (DOF) of at least 20 mm (T14) are the minimum advantageous requirements for iHSI [33] but an even more advantageous scenario includes a system capable of variable WDs, FOVs and DOFs in order to maximise compatibility with current surgical visualisation systems [34]. The number of spectral bands, spectral range and spatial image definition largely depend on the clinical application to provide the critical functional and/or semantic features. Based on reviewing the previous literature and our own experience, providing tens of well-defined spectral bands is advantageous to achieve significant improvement with respect to standard RGB imaging. Based on the availability of industrial state-of-the-art snapshot HSI sensors (cf. Table 3), exemplar embodiment achieving advantageous requirements for an iHSI system during surgery may provide 16 spectral bands (T15) and a spectral range of at least 160 nm (T16). Other exemplar embodiments make use of at least 100 spectral bands with at least 500 nm spectral coverage (cf. Table 3), albeit at a lower frame rate, and may advantageously achieve superior tissue differentiation functionality. With the advantageous goal of providing information with at least 1 mm precision, exemplar embodiments would achieve at least 3 pixels per millimetre. Exemplar embodiments achieving the minimum advantageous and advantageous target FOV requirements incorporate imaging grids of at least 120×120 and 450×450. However, based on currently available HSI sensor technology, substantially higher resolutions are possible. Hence, exemplar embodiments advantageously target the resolutions of high-definition (1920×1080 pixels) and ultra high-definition (3840×2160) for advantageous minimum and target advantageous requirements, respectively (T17). Image calibration advantageously supports the generation of interpretable HSI data. Typical embodiments include the acquisition of both a white and dark reference image for white balancing to account for ambient light and specific camera settings (T18). As means of example, this can typically be achieved by acquiring images using a white reflectance tile and with a closed shutter, respectively. However, for surgical guidance in the OR, calibration data should advantageously be available without having to interrupt the clinical workflow.

The minimum advantageous imaging rate benefits from being fast enough to provide real-time information suitable for surgical decision making without interfering with the surgical workflow (T19). Based on speed of processing in the human visual system an image visualisation rate faster than 7 frames per second (FPS) is advantageous [35]. In some scenarios with a static scene, image acquisition rates of a few seconds per image per surgical scene may be sufficient to provide critical information to the surgical team. However, iHSI suitable for real-time image-guided surgery should advantageously be capable of providing video-rate imaging to provide a live display of tissue information that allows also for dynamic scenes during surgery. Intraoperative HSI System Design.

By following the system design requirements above, we propose an iHSI system embodied and shown in FIG. 5. An HSI camera can advantageously be connected to a sterile optical scope via an appropriate eye-piece adapter. The sterile optical scope can advantageously be connected to the light source via a sterile light guide.

The following are some particular aspects, features, and advantages of embodiments according to the present disclosure.

1. Use of a surgical exoscope in combination with HSI camera for real-time tissue characterisation to augment the surgeon's vision and aid intraoperative decision-making. In some embodiments, the sterile optical scope may be an exoscope but could also be an endoscope or surgical microscope.
2. Embedding of optical filters into the HSI camera head for effective signal filtering proximal to the HSI camera sensor for high-fidelity data capture. In some embodiments, optical filters can advantageously be added in the eye-piece adapter to acquire high-fidelity hyperspectral imagery while allowing for a compact optical system.
3. Tailored optical filter arrangements are used to account for quantum efficiency differences of individual band sensors and obtain equalized sensor responses across all band sensors. In some examples, this may include the use of tailored optical filter arrangements to account for quantum efficiency differences of individual band sensors and obtain equalized sensor responses across all band sensors for signal processing.
4. Filter-embeddings to allow on-the-fly image calibration during surgery. Deliberate changes to the optical path may be performed by adjusting optical filter arrangements for on-the-fly image calibration during surgery given a target with known reflectance properties. In some embodiments, these filter adjustments may be performed using a filter wheel in the light source.
5. Use of infinity-corrected modules to maintain identical beam focusing at the HSI camera sensor plane for multiple filter arrangements. In some examples, infinity-corrected modules may be used to create parallel light beam between the objective lens and tube lens. It will allow to add parallel flat optical elements (e.g. filters) without changing the parfocal point thus not create any image shifts.
6. Custom attachment for telescope to interlock optical system components to prevent sliding, rotation or any other changes to prevent undesired optical property changes to the optical system during surgery. Optical system components including filters, telescopes, and optical lenses, may be mechanically locked to prevent undesired optical property changes to the optical system during surgery. In some embodiments, this may include the use of custom attachments, such as triangular or other geometrically shaped connectors, to mechanically lock optical components and prevent sliding, rotation or any other changes to maintain desired optical properties for image calibration and processing.
7. Custom light-splitters divide light into spectrally separated beams to acquire multiple sub-images on a single or multiple HSI sensors. Custom light splitters may be used to divide light into spectrally-separated beams to acquire multiple sub-images on a single or multiple HSI sensors. In some embodiments, beam splitting may be achieved using a microlenses array or a prism, such as a Wollaston prism, to split a single beam into two or more sub-images on the same sensor. Advantageously, different optical filters may be used for different beams to acquire hyperspectral imagery. The use of hyperspectral sensors with multiple modes of spectral response can advantageously be combined with such multiplicity of filters to generate response targeting a different subset of spectral modes irrespective of the use of a single or multiple sensors.
8. High-frequency light source switching to detect and discern ambient light contributions from the acquired HSI data. Controlled high-frequency on-and-off switching of the light source may be used to detect and discern ambient light contributions from the acquired HSI data. Synchronisation between light source switching and HSI camera acquisition may be achieved using a separate trigger mechanism such as a separate cable connection.
9. Heat dissipation measures suitable for surgical setup to ensure low-noise imaging and safe handling for the operator. Additional heat dissipation measures for the draped camera system, including active and passive cooling mechanisms, may be applied to ensure low-noise imaging and safe handling for the operator. In some embodiments, this may include the provision of heat sinks directly attached to the camera. In other embodiments, this may include ensuring thermal conductivity between the camera and a mechanical arm or stand used to help the imaging system in place.

Besides connecting the scope with the camera, an eye-piece adapter may provide a control mechanism for zooming and focusing. Filters may be placed in the optical path anywhere in between the origin of the travelling light and its receiving end such as the camera sensor. In some embodiments, optical filters can be placed in a filter wheel embedded in the light source to restrict the light source spectrum depending on the camera sensor or clinical requirements.

The HSI camera may be connected to a computational workstation or equivalent device via a connection that provides both power and a fast data link suitable for real-time HSI data transfer. The workstation or equivalent device processes the acquired HSI data for real-time visualisation of derived information. A sterile surgical drape, covering both the HSI camera and data cable, may be sealed with the sterile exoscope ensuring sterility of the overall imaging system.

Depending on the surgical application, the sterile imaging system may be hand-held by the operator or fixed to a surgical table using a standard mechanical arm permitting controlled mobilisation or immobilisation of the imaging system depending on the clinical requirements during surgery. In some embodiments where the camera system is lightweight enough, its controlled mobilisation and immobilisation can be achieved by using a sterile or draped mechanical arm that attaches to the sterile optical scope. Such a mechanism allows positioning of the iHSI system at a safe distance outside the surgical cavity while the eye-piece adapter provides appropriate focusing capabilities for acquiring HSI data. Other embodiments may include the use of a robotic positioning arm to hold and control the imaging device.

Figure 11:
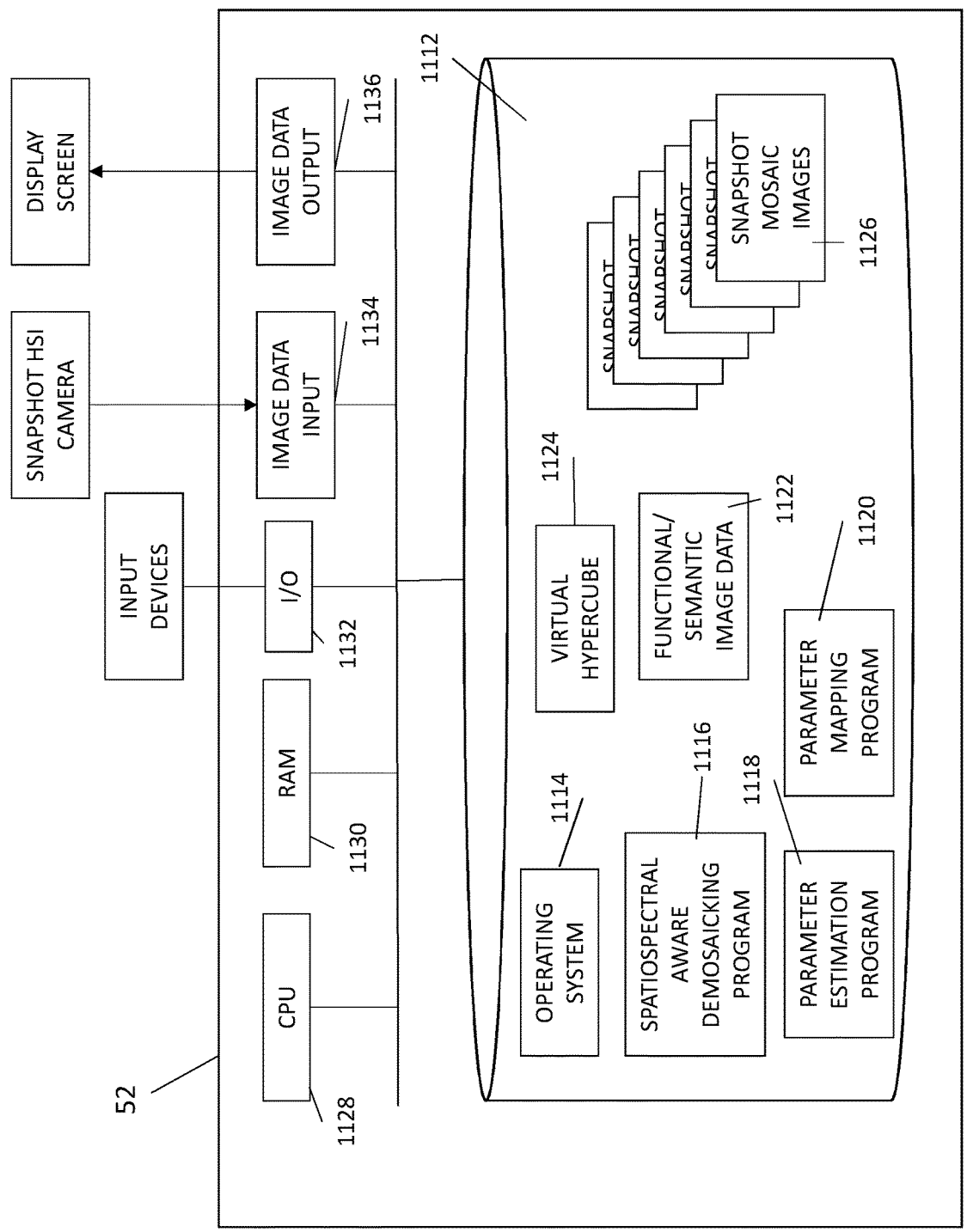
FIG. 11 is diagram of a computer system according to an embodiment of the invention.

Computational steps are performed by a computation workstation 52 to extract tissue or object property information on a per pixel-level from acquired low-resolution snapshot hyperspectral imaging data for display during surgery. The computations workstation 52 is shown in more detail in FIG. 11, from where it can be seen that the computation workstation 52, which may be a suitably programmed general purpose computer, comprises a processor 1128, provided with memory 1130, and an input-output interface 1132 from which control inputs can be obtained from peripheral devices such as keyboards, footswitches, pointing devices (such as a computer mouse or trackpad), and the like. In addition, a further input port 1134 has connected to it a hyperspectral imaging camera for capturing hyperspectral imaging data, and an image data output port 1136 is connected to a display, for displaying images generated by the present embodiment, using the hyperspectral imaging data as input.

Also provided is a computer readable storage medium 1112, such as a hard disk, solid state drive, or the like, on which is stored appropriate control software and data to allow embodiments of the invention to operate. In particular, the storage medium 1112 has stored thereon operating system software 1114, which provides overall control of the computing system 52, and also has stored thereon spatiospectral demosaicking program 1116, and parameter estimation program 1118. In addition, parameter mapping program 1120 is also provided. As will be described later, the spatiospectral demosaicking program 1116, and parameter estimation program 1118 operate together to provide a first embodiment, whereas the parameter mapping program operates to combine the functionality of the spatiospectral demosaicking program 1116, and parameter estimation program 1118 into a single process to provide a second embodiment. Input to both embodiments is in the form of multiple snapshot mosaic images 1126, and the output is various functional or semantic data images 1122, as will be described. In addition, an intermediate data structure in the form of virtual hypercube 1124 may also be stored on the computer readable medium, which is generated during the operation of the first embodiment, as will be described.

Detailed Description of Embodiments Relating to a HSI Method

Hyperspectral information of an object, such as tissue, is affected by spatiospectral parasitic effects in addition to spatiospectral downsampling during snapshot imaging which leads to the acquisition of a hyperspectral image that is characterised by low spatial and low spectral resolution. The disclosed methods may perform computational steps that address each of these effects either independently or jointly to obtain per-pixel estimates of tissue or object property information in high spatial resolution.

A filter response mapping may be used to describe hyperspectral information of an object in lower spectral resolution acquired by individual band sensors of the snapshot imaging sensor. Further band selection and crosstalk modelling approaches may be used to describe the acquired low-spectral and low-spatial resolution snapshot mosaic image.

In some embodiments (i.e. the first embodiment mentioned above), hyperspectral information of a virtual hypercube characterised by low spectral but high spatial resolution may then be reconstructed by deploying spatiospectral correction approaches. Computational parameter estimation approaches may be used to infer per-pixel tissue or object properties. Example computational approaches are disclosed below.

In other embodiments (i.e. the second embodiment mentioned above), tissue or object property information can be obtained from the acquired low-resolution snapshot data directly. Example computational approaches are disclosed below.

It should be clear to a person skilled in the art, that a direct parameter estimation approach can be considered as the inference of tissue-property information from a virtual hypercube where the reconstructed virtual hypercube itself corresponds to the estimated tissue property map. Further details will be provided with respect to FIG. 6.

Figure 6:
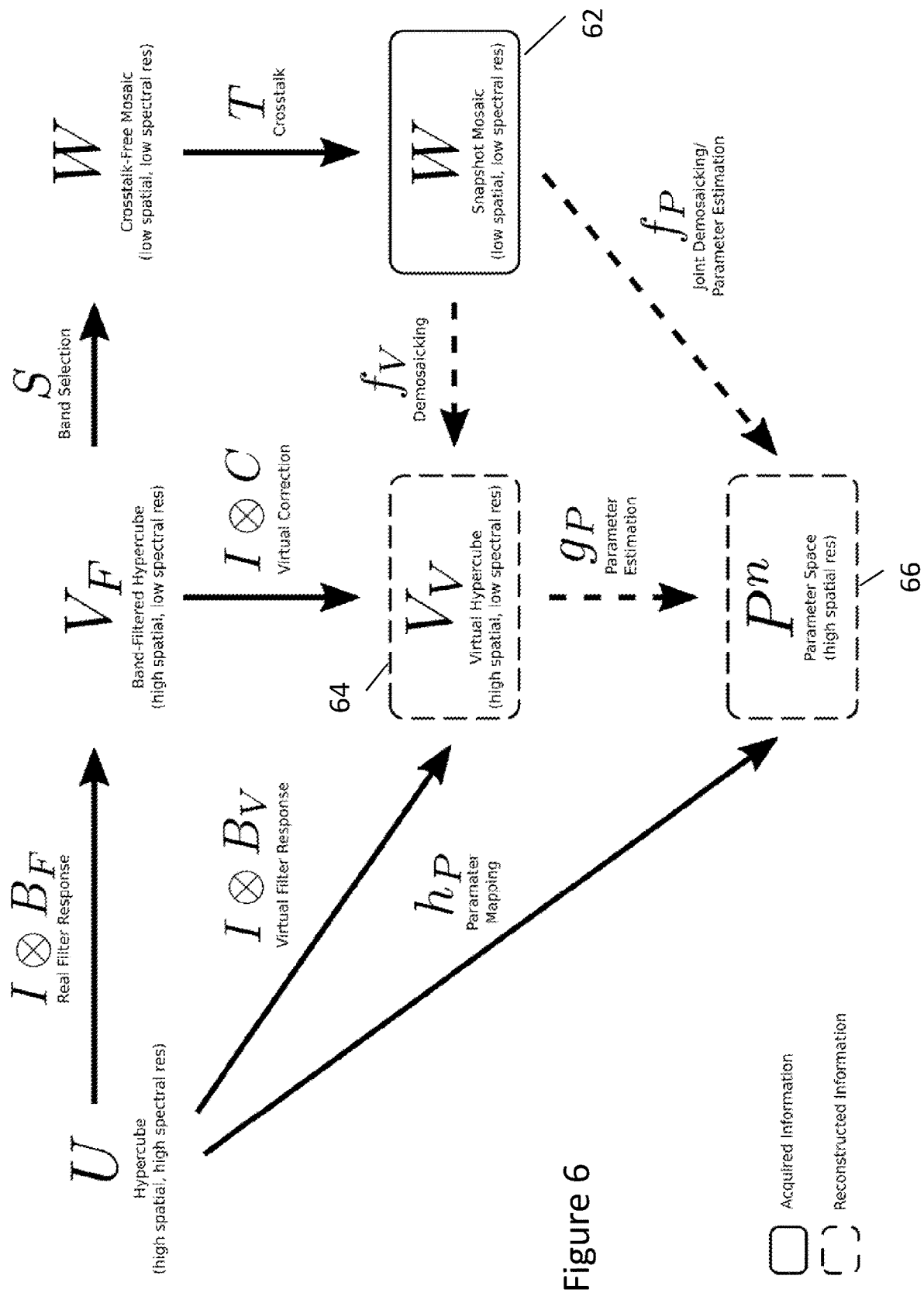
FIG. 6 is a commutative diagram representing the steps the computational methods perform during spatiospectral calibration, virtual hypercube reconstruction and parameter estimation.

FIG. 6 presents an overview of the involved steps the computational methods of both the first and second embodiments may perform. In summary, in the first embodiment snapshot mosaic data w is captured at 62, with low spatial and low spectral resolution. This then undergoes a demosaicking process to generate a virtual hypercube 64, containing virtual high spatial, but low spectral resolution data. From the virtual hypercube a parameter estimation process can then be performed, as detailed further below, to obtain desired high spatial resolution data 66 in the desired parameter space.

In contrast, for the second embodiment the snapshot mosaic data W is again captured at 62, with low spatial and low spectral resolution. This is then subjected to a joint demosaicking and parameter estimation process, which strictly speaking foregoes the complete generation of a virtual hypercube (although conceptually might be thought of as still generating the parts of it that are required, even if in fact the computation is performed more directly) as detailed further below, to obtain desired high spatial resolution data in the desired parameter space directly.

In more detail, for real-time hyperspectral imaging, sparse hyperspectral information may be obtained by using a snapshot camera system that simultaneously acquires individual bands at different spatial locations using a sensor array of mosaic filters in 'one shot'. Such a system may acquire a snapshot mosaic image on a regular grid $w \in W := \mathbb{R}^{n_x} \times \mathbb{R}^{n_y}$ with active sensor area W of width $n_x$ and height $n_y$. It shall be noted that alternative sensor types with irregular or systematic pixel arrangements similar to mosaic imaging, such as tiled capturing using microlens arrays (FIG. 2), can be addressed by straightforward adaptation of the following approaches.

A snapshot mosaic w E w describes a 'flattened', two-dimensional (2D) and low-resolution approximation of a, typically unknown, three-dimensional (3D) high-resolution hypercube $u \in U := W \times \mathbb{R}^{n_A}$ with $n_A \in \mathbb{N}$ discrete bands of the optical spectrum providing an approximation of the continuous optical spectrum in a wavelength range of interest.

Figure 7:
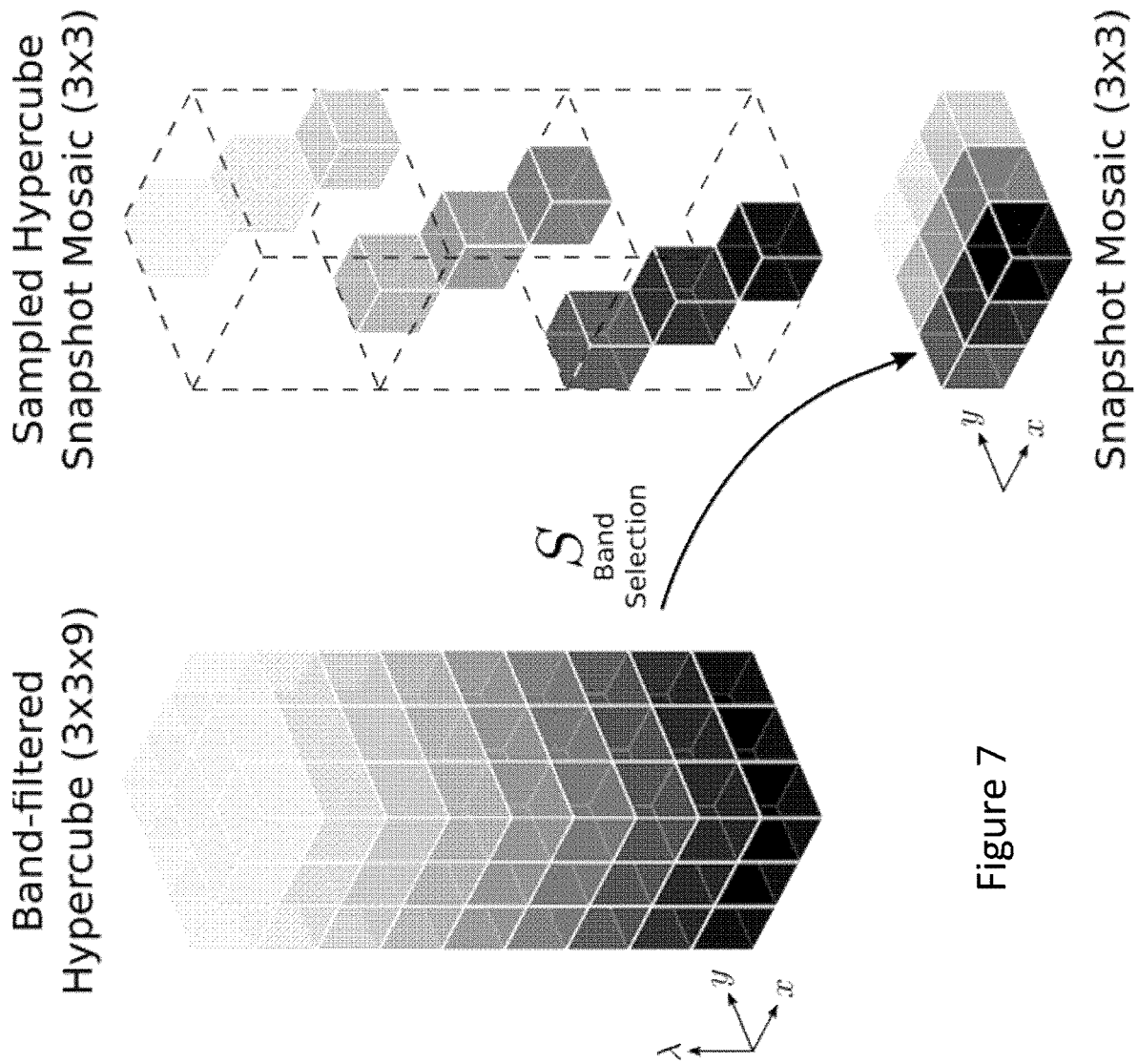
FIG. 7 is a display that schematically compares the sparse hyperspectral information acquired in a two-dimensional snapshot mosaic image with the information captured in a three-dimensional hypercube.

For an example of an $m_1 \times m_2$ mosaic filter, a total of $m_1 m_2$ individual spectral bands may be acquired over an $m_1 \times m_2$ spatial region. For an $m_1 \times m_2$ mosaic, a filter response operator $B_F: \mathbb{R}^{n_A} \to \mathbb{R}^{m_1 m_2}$ may be assumed that describes the mapping from $n_A$ to all the $m_1 m_2$ discrete bands of the optical spectrum whereby $m_1 m_2 << n_A$ typically. This operator shall advantageously model the spectral response of the respective filters including the relative radiance of the light source, higher-order harmonics and spectral leakage of the mosaic filters but no spatial cross-talk across the sensor elements, which will be accounted for separately. Assuming the independent application of such filter band responses to all individual spatial locations in the active sensor area W a hypercube $u \in U = w \times \mathbb{R}^{n_A}$ can be transformed into a hypercube $v \in V_F := W \times \mathbb{R}^{m_1 m_2}$ with lower spectral resolution via $B_F$. By assuming identical properties of all mosaic filters, the extension of the filter response operator $B_F$ to the active sensor area can be formally described using the Kronecker product $\otimes$ in combination with the identity operator I, i.e. $I \otimes B_F: U \to V_F$ with $(I \otimes B_F)(u) = v$. Defining a band selection operator $$S_{\mathbb{R}^{m_1} \times \mathbb{R}^{m_2}} : \mathbb{R}^{m_1} \times \mathbb{R}^{m_2} \times \mathbb{R}^{m_1 m_2} \to \mathbb{R}^{m_1} \times \mathbb{R}^{m_2},$$

the mapping from a mosaic hypercube to a snapshot mosaic can be described, i.e. the 'flattening' of a three-dimensional $m_1 \times m_2 \times m_1 m_2$ hypercube onto a two-dimensional $m_1 \times m_2$ mosaic that contains the spectral information of each of the individual $m_1 m_2$ acquired bands at different $m_1 m_2$ spatial positions (FIG. 7). This operation can be naturally extended to a selection operator S: $=S_w$: $W \times \mathbb{R}^{m_1 m_2} \to W$ over the entire active sensor area w. Spatial cross-talk between individual neighbouring band sensors is modelled by an appropriate cross-talk operator T: $=T_w$: $W \to W$ over the active sensor area w of the sensor. As an example, a convolution with kernel size k×k may be assumed to model the cross-talk around a k×k neighbourhood per pixel. By introducing a spatial cross-talk operator T that accounts for mixed sensor responses of neighboring filters, all remaining, primarily spectral, parasitical effects are therefore accounted by the spectral filter response operator $B_F$. Overall, the forward model of the snapshot mosaic image acquisition that independently accounts for spatial and spectral leakages of the imaging system can be described by the joint operator $$T \cdot S \cdot (I \otimes B_F) : U \to W, \quad (1)$$

which maps the (typically unknown) 3D high-resolution hypercube $u \in U$ into the 2D low-resolution snapshot mosaic $w \in W$. Specific examples of how to obtain both the real spectral filter response operator $B_F$ and the spatial cross-talk operator T of the mosaic sensor to characterise the hyperspectral snapshot imaging setup are shown below. To account for differences in the optical spectrum provided by different light sources, white balancing may be performed for acquired radiances $w \in W$ as a preprocessing step or its impact may be embedded in $B_F$.

Figure 8:
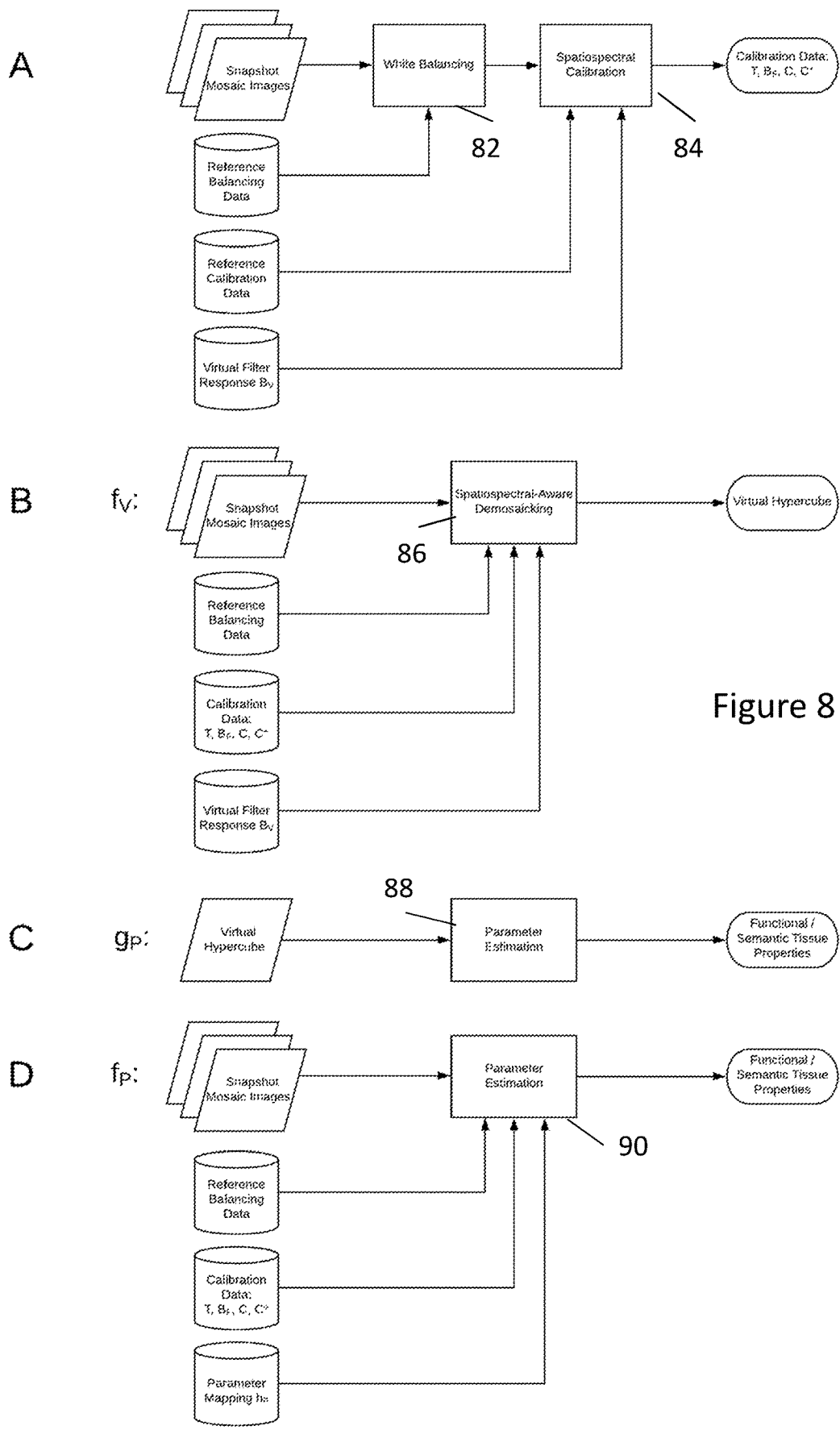
FIG. 8 is a diagram describing the steps of spatiospectral calibration, spatiospectral-aware demosaicking, and parameter estimation via virtual hypercubes or acquired snapshot imaging data.

Similar to the filter response operator $B_F$: $\mathbb{R}^{n_\lambda} \to \mathbb{R}^{m_1 m_2}$ for a given mosaic sensor, a virtual filter response operator $B_V$: $\mathbb{R}^{n_\lambda} \to \mathbb{R}^{n_\lambda}$ for $n_\lambda$ virtual bands can be defined. Virtual filter responses can be chosen depending on the desired task. Specific choices of the virtual filter responses may include representations of idealised transfer functions of optical filters, such as the primary response of Fabry-Perot optical resonators, which are characteristic of some snapshot imaging systems such as presented by Pichette et al., *Proc. of SPIE*, 2017. Virtual bands may also be chosen as regularly spaced spectral bands for increased interpretability and interoperability. Other examples include the spectrum of end-members that are of particular interest for tissue property extraction, such as Hb or $HbO_2$ (FIG. 4). In practice, the number of virtual filter bands n, may be smaller or equal than the number of filter bands $m_1 m_2$ of the mosaic sensor. By introducing an operator C: $\mathbb{R}^{m_1 m_2} \to \mathbb{R}^{n_\lambda}$ for spectral correction, a spectral mapping from real to virtual filter responses of the system can be established by ensuring $C \cdot B_F \approx B_V$. Specific examples of how to obtain the spectral calibration operator C are shown below (FIG. 8A). In cases where the spectral responses of the acquisition filters include a limited or null amount of spectral parasitical effects such as higher-order harmonics and spectral leakage, it may be advantageous to choose $B_V = B_F$ thus leading to C describing the identity operator.

With the definition of a virtual hypercube space $V_V := W \times \mathbb{R}^{n_\lambda}$, spatiospectral-aware 'demosaicking' or 'upsampling' $f_V$: $W \to V_V$ then refers to the reconstruction of a virtual hypercube $v \in V_V$ from an acquired snapshot image $w \in W$, i.e. $f_V(w) = v$, which accounts for both spatial cross-talk and spectral parasitical effects. Specific examples of demosaicking approaches $f_V$ are shown below (FIG. 8B).

Based on a reconstructed virtual hypercube $v \in V_V$ parameter estimation approaches $g_P$: $V_V \to P^n$ can be used to estimate image property information on a pixel level over the entire active sensor area, i.e. to estimate a property $p \in P^n := W \times \mathbb{R}^n$ whereby $n \in \mathbb{N}$ depends on the type of property (FIG. 8C). For example, n=1 may be used for semantic tissue classification for the differentiation between benign and malignant tissue types whereas n=3 may be used for the estimation of pseudo-RGB images.

Instead of individual demosaicking and parameter extraction steps, i.e. $p = g_P(v) = g_P(f_V(w))$, joint models $f_P$: $W \to P^n$ are presented to allow an end-to-end approach directly from the acquired mosaic images $w \in W$ (FIG. 8D).

As should be clear to a person skilled in the art, all computational methods may also be used for multiple camera systems that provide multiplexed video stream data. Additionally, all presented computational approaches may lead to reconstructions on a different high-resolution grid other than then the active sensor area W. All computational methods may also be based on any other positive loss functions (e.g. smooth L1 or bisquare) other than the norm presented in the examples. Specific assumptions on the noise level for error estimates may also be made, such as the assumption that noise is independent but not identically distributed across wavelengths.

White Balancing

An acquired mosaic image captures the radiance from an object. Reflectance calculation, or white balancing, may be performed to compute the reflectance signal from the acquired radiance in the snapshot mosaic image $w \in W$ as a preprocessing step. This may be achieved by using separately acquired reference images, including white and dark reference mosaic images $w_{d;\tau_d}$ and $w_{w;\tau_w}$ acquired at integration times $\tau_d$ and $\tau_w$, respectively. In some examples, white balancing may be achieved by deploying a linear model. I.e. in addition to the acquired mosaic image $w_\tau$ of an object with integration time $\tau$, a white reference mosaic image $w_{w;\tau_w}$ of a reflectance tile with integration time $\tau_w$, and dark reference mosaic images $w_{d;\tau}$ and $w_{d;\tau_w}$ acquired with integration times $\tau$ and $\tau_w$, with a closed shutter, white balancing yields the reflectance mosaic image $$r := \frac{w_\tau - w_{d;\tau}}{w_{w;\tau_w} - w_{d;\tau_w}} \frac{\tau_w}{\tau} \in W. \quad (2)$$

For some examples, integration times $\tau$ and $\tau_w$ in (2) may be identical. In others, $\tau_w$ may be reduced to avoid potential sensor saturation effects. As should be clear to a person skilled in the art, the white reference may also refer to any means of acquiring a preferably spectrally neutral reference. In some embodiments, the use of a grey card may for example be combined with an intensity correction factor akin to the effect of $\tau_w$ so as to avoid any potential saturation effects when acquiring the white reference. A sterile imaging target with known reflectance characteristics, such as medical equipment available in the operating theatre, may also be used to estimate a white reference according to (2). An example of such sterile imaging target may be a surgical gauze. Specular reflections of one or more acquired images, obtained from various angles and positions to the surgical scene, may also be used as a surrogate of a white reference signal.

In examples where imaging setup characteristics are known a priori, white balancing may be precomputed therefore removing the need of acquiring white and dark references in an intraoperative setup. Both white and dark references may be estimated in-factory for a variety of camera settings to be used for on-the-fly white balancing during intraoperative use of the imaging system.

White balancing according to (2) may also be performed for fluorescence imaging applications. This may include white balancing of the system in conjunction with optical components specifically designed for fluorescence-based imaging, such as an exoscope with adequate light source and optical filters for indocyanine green (ICG) or 5 aminolevulinic acid (5-ALA) induced protoporphyrin IX (PpIX).

All presented white balancing approaches may include the temporal processing of a video stream. Such approaches may be used to account for measurement uncertainty or to capture spatially varying white balancing with non-uniform reflectance targets, such as a surgical gauze. Examples may include the temporal averaging of the white or dark reference images used for (2).

Spatiospectral Calibration

Both the real spectral filter response operator $B_F \in \mathbb{R}^{m_1 m_2 \times n_\Lambda}$ and the spatial cross-talk operator T: W→W in (1) can be estimated in a controlled setup to account for parasitical effects during image acquisition.

By measuring the characteristic of the sensor in-factory a measured system filter response operator $A_F^{meas}$: U→W can be obtained. This may be achieved by acquiring snapshot mosaic image data using collimated light and sweeping through all $n_\Lambda$ wavelengths in conjunction with an imaging target with known, typically spatially-constant, spectral signature. In conjunction with (1), spatiospectral calibration of the imaging system may then be performed.

In the example of linear operators $B_F$: $\mathbb{R}^{n_\Lambda} \to \mathbb{R}^{m_1 m_2}$ and T: W→W, let $\theta_T \in \mathbb{R}^{m_1 m_2 k^2}$ denote the unknown parameters of a cross-talk operator T describing k×k convolution kernels for the $m_1 m_2$ filters to model the mixing of pixel neighbourhood responses for each band. Spatiospectral calibration of the imaging system can be performed by estimating, in (1), both $B_F$, represented in this linear operation mode as a matrix in $\mathbb{R}^{m_1 m_2 \times n_\Lambda}$, and T, represented with $\theta_T$, by solving an optimisation problem such as $$\min_{\theta_T \in \mathbb{R}^{m_1 m_2 k^2}} \min_{B_F \in \mathbb{R}^{m_1 m_2 \times n_\Lambda}} \|T(\cdot; \theta_T) \circ S \circ (I \otimes B_F) - A_F^{meas}\|. \quad (3)$$

Additional regularisation and constraints, such as positivity constraints, on the variables may be applied for $\theta_T$ and/or $B_F$ in (3). In some embodiments, a model using the same kernel for each band may for example be advantageous. In some examples, further regularisation may include the use of a blind source separation approach which may result into an optimization problem of the form $$\min_{\theta_T > 0} \min_{B_F \geq 0} \sum_{i,j=1}^{m_1 m_2} Sim(B_F(i,\cdot), B_F(j,\cdot)) \quad (4)$$

such that $\|T(\cdot; \theta_T) \circ S \circ (I \otimes B_F) - A_F^{meas}\| < \varepsilon$ for a given error threshold $\varepsilon > 0$ and a similarity measure Sim. Similarity measures may include normalized mutual information, Kullback-Leibler divergence, or other existing scores. Alternatively, one may be interested in minimising the deviation, measured by a function Dev, from an expected model as can be done for example using a normality testing score:

$$\min_{\theta_T > 0} \min_{B_F \geq 0} \sum_{i=1}^{m_1 m_2} Dev(B_F(i,\cdot)) \quad (5)$$

such that $\|T(\cdot; \theta_T) \circ S \circ (I \otimes B_F) - A_F^{meas}\| < \varepsilon$ It should be clear that reformulation of such constrained optimisation models can be done by relaxing the hard constraints through the inclusion of additional regularisation terms in (3).

From (3) it follows that for other examples spatiospectral calibration for an intraoperative system may be performed by acquiring snapshot mosaic images $w \in W$ of an object with known hypercube $u^{ref} \in U = W \mathbb{R}^{n_\Lambda}$ over a spatial region $\Omega \subset W$, i.e. $u^{ref}|_{\Omega \times \mathbb{R}^{n_\Lambda}}$ is known. This leads to a spatiospectral calibration problem of the form $$\min_{\theta_T \in \mathbb{R}^{m_1 m_2 k^2}} \min_{B_F \in \mathbb{R}^{m_1 m_2 \times n_\Lambda}} \|(T(\cdot; \theta_T) \circ S \circ (I \otimes B_F))|_\Omega (u^{ref}) - w|_\Omega\| \quad (6)$$

where additional regularisation and variable constraints may be applied, such as mentioned above.

Besides commercial calibration targets, a sterile imaging target with known reflectance characteristics, such as medical equipment available in the operating theatre, may be used to define $u^{ref}$ for (6).

The initialisation of $B_F$ in (3)-(6) may be performed based on the measured system filter response operator $A_F^{meas}$. One advantageous embodiment being to perform such initialisation with data acquired in factory and then performing refinement using data acquired at the point of care.

Calibration of the optical system during a surgical setting using (6) may be achieved using different optical filters with optical transmission properties $t \in \mathbb{R}^{n_\Lambda}$. For example, for a target with known hypercube representation $u^{ref} \in W \mathbb{R}^{n_\Lambda}$ over a region $\Omega \subset W$, (6) can be solved for $t \odot u^{ref}$ and resulting snapshot mosaic image $w_t$, whereby $\odot$ denotes the pointwise multiplication in the spectral dimension. Advantageously, switching across t can be implemented through the activation of a filter wheel embedded in the light source of the imaging system.

Calibration of the optical system during a surgical setting using (6) may also be achieved via the temporal processing of a video stream to account for measurement uncertainty or to enable the use of spatially-varying non-uniform reflectance targets, such as a surgical gauze, for white balancing. An example may include the temporal averaging of acquired snapshot images w of a target with known average reflectance characteristics.

Given virtual filter responses $B_V$: $\mathbb{R}^{n_\Lambda} \to \mathbb{R}^{n_\Lambda}$, a mapping between band-filtered and virtual hypercube spaces $V_F = W \times \mathbb{R}^{m_1 m_2}$ and $V_V = W \times \mathbb{R}^{n_\Lambda}$ can be established by finding a spectral correction operator C: $\mathbb{R}^{m_1 m_2} \to \mathbb{R}^{n_\Lambda}$ such that $C \cdot B_F \approx B_V$. In case of linear operators represented as matrices, this leads to $$C := \min_{\tilde{C} \in \mathbb{R}^{n_\Lambda \times m_1 m_2}} \|\tilde{C} \ B_F - B_V\|, \quad (7)$$

whereby additional regularisation may be performed.

It is worth noting that the calibration computation in (7) reduces to the method described in *Pichette et al., Proc.* of SPIE, 2017 if and only if the spatial cross-talk operator T is assumed to be the identity operator, $n_\lambda = m_1 m_2$ and all $m_1 m_2$ bands are acquired at the same spatial location which is not the case for snapshot mosaic imaging when imaging spatially-varying scenes (FIG. 7). Moreover, no demosaicking steps that account for both spatial cross-talk and spectral parasitical effects were presented in Pichette et al., Proc. of SPIE, 2017..

For spatiospectral-aware demosaicking, it may be useful to estimate the pseudo-inverse of the spectral correction operator instead, i.e.

$$C^\dagger := \min_{\tilde{C} \in \mathbb{R}^{m_1 m_2 \times n_\lambda}} \|\tilde{C} \; B_V - B_F\|, \qquad (8)$$

whereby regularisation may be performed. In other examples, C and $C^\dagger$ may be obtained as a result of using invertible neural networks as a model for C in (7).

As should be clear to the person skilled in the art, all calibration methods described in here may be performed for multiple camera set-ups including different acquisition settings such as different gains.

Spatiospectral-Aware Demosaicking

Spatiospectral-aware demosaicking methods $f_V: W \to V_V$ aim at reconstructing a virtual hypercube $v \in V_V = W \times \mathbb{R}^{n_A}$ from an acquired mosaic image $w \in W$, i.e. $v = f_V(w)$, by accounting for parasitical effects present in snapshot imaging.

Figure 9:
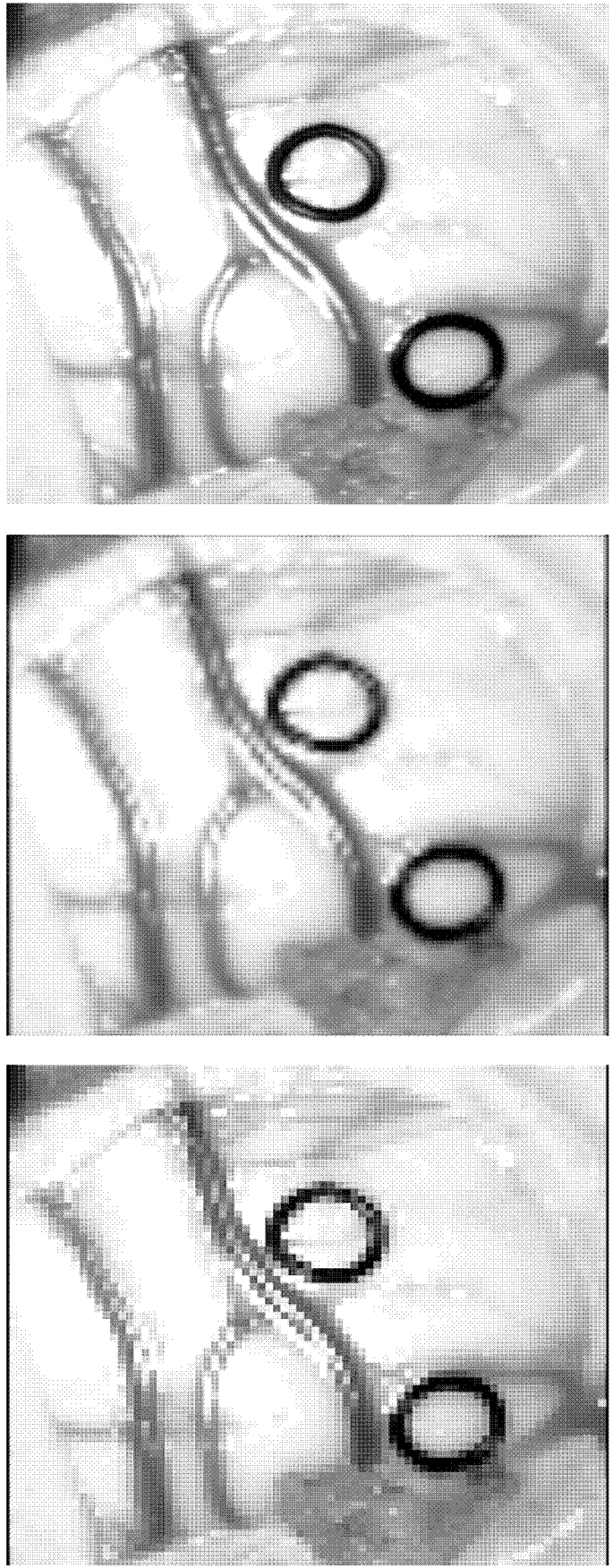
FIG. 9 is a display illustrating the shortcomings of demosaicking using methods with no spatiospectral awareness.

A straightforward and computationally fast approach for demosaicking may be to use image resampling, such as linear or cubic resampling, on the calibrated mosaic images followed by the application of the spectral calibration matrix C in (7). In absence of a model that takes into account spatial and spectral parasitical effects, this leads to a hypercube reconstruction that suffers from blur in both spatial and spectral dimensions as well as other artefacts such as edge shifts and therefore leads to increased uncertainty for subsequently performed tissue characterisation (FIG. 9).

With the forward model $$A_V := T \cdot S \cdot (I \otimes C^\dagger): V_V \to W \qquad (9)$$

a regularised inverse problems (IP)-based demosaicking approach $f_V^{IP}$ may be described as $$f_V^{IP}(w) = \mathrm{argmin}_{v \in V_V}(\|A_V v - w\| + Reg_{IP}(v)) \qquad (10)$$

with an appropriate regularisation operator $Reg_{IP}$, such as Tikhonov regularisation, and constraints on the variables, such as positivity constraints.

Depending on the choice of the virtual filter responses $B_V$, (8) and, thus, (10) may be of a very ill-posed nature. Alternative examples for IP-based demosaicking may include the minimisation of $$v^*_F = \mathrm{argmin}_{v \in V_F}(\|(T \cdot S)v - w\| + Reg_{IP}(v)) \qquad (11)$$

instead which leads to $$f_V^{IP}(w) = (I \otimes C)v^*_F. \qquad (12)$$

Additional regularisation and variable constraints may be applied in (8), including a regularisation of the form $Reg_{IP}((I \otimes C)v)$ instead of $Reg_{IP}(v)$.

For increased computational efficiency, all operators may be implemented as matrix-free operators.

If linear modelling with Tikhonov regularisation is used in combination with an $\ell^2$- norm, dedicated linear least-squares method, such as LSMR, may be deployed to solve (10) or (11). In case of total variation-based regularisation, alternating direction method of multipliers (ADMM) may be used. Other numerical approaches, such as primal-dual or forward-backward splitting algorithms, may be used instead depending on the type and combination of operator models, data loss and regularisation terms.

To obtain fast computational times for spatiospectral-aware demosaicking for real-time intraoperative guidance during surgery, machine learning approaches may be used where fast computational times at inference can be achieved at the cost of slower computational times at training stage. The implementation of a machine learning approach may be based on a fully convolutional neural network (CNN). In some examples, the CNN may be implemented using a U-Net-like architecture.

Supervised (S) machine learning approaches for spatiospectral-aware demosaicking $f_V^S(\cdot; \Theta): W \to V_V$ with model parameters $\Theta$ may be deployed in case a database of paired samples, i.e. $\{(w_j, v_j)\}_{j \in J}$, is available. As one example, optimal parameters $\Theta^*$ could be established by minimising the expectation a loss function $\ell: V_V \times V_V \to \mathbb{R}^+$, i.e. the risk or generalization error. A straightforward approach of this may be based on empirical risk minimisation for a training subset $J_T \subset J$ using the loss $\ell(v_1, v_2) = \|v_1 - v_2\|$, i.e.

$$\Theta^* := \mathrm{argmin}_\Theta \left( \sum_{j \in J_T} \|f_V^S(w_j; \Theta) - v_j\| + Reg_S(\Theta) \right) \qquad (13)$$

with an appropriate regularisation operator $Reg_S$. It should be clear that any other loss e may be used in (13) in addition to approaches that increase generalizability, including stopping the optimization when a loss criteria is reached on a separate validation data set, using data augmentation strategies, drop-out and the like. In case no paired database is readily available, such a training database may also be constructed using classical IP-based approach as $\{(w_j, f_V^{IP}(w_j))\}_{j \in J}$. In other embodiments, a paired database may also be constructed by simulating snapshot data from existing hypercube data via the forward model (9), i.e. $\{(A_V v_j, v_j)\}_{j \in J}$.

In other examples, an unsupervised (U) machine learning approach $f_V^U(\cdot; \Theta): W \to V_V$ with model parameters $\Theta$ may be deployed for a database $\{w_j\}_{j \in J}$. An example may include a self-supervised approach by finding optimal parameters $\Theta^*$ such that it holds for a training subset $J_T \subset J$ $$\Theta^* := \mathrm{argmin}_\Theta \left( \sum_{j \in J_T} \|A_F f_V^U(w_j; \Theta) - w_j\| + Reg_U(\Theta) \right) \qquad (14)$$

with an appropriate regularisation operator $Reg_U$. In some embodiments, regularisation may also be based on cycle consistency losses.

In other embodiments, semi-supervised machine learning approaches may be used in case no exhaustive, or no sufficiently representative/realistic, database of paired examples is available. A typical implementation of such approach could rely on a formulation combining supervised and unsupervised losses from (13) and (14). Examples may also include the use of adversarial training approaches, such as the use of generative adversarial networks (GANs), to increase the dataset by synthesizing high-fidelity data pairs from available data.

Implementations of these examples may include the use of deep neural networks such as CNNs. An example may be based on a single-image super resolution reconstruction network architecture based on a residual network structure, whereby the initial upscaling layer takes into account the regular, but spatially shifted hypercube sampling reflected in the mosaic image acquisition. Other approaches may use input layers suitable for irregularly sampled input data, such as layers based on Nadaraya-Watson kernel regression.

Temporally-Consistent Demosaicking

Instead of reconstructing a virtual hypercube from a single mosaic image at a time, a temporally-consistent approach may be deployed for increased robustness.

Spatiospectral-aware demosaicking for temporally-consistent virtual hypercube reconstruction between two or more consecutive frames may be used and based on motion compensation in between frames.

Inverse problems-based approaches for temporally-consistent spatiospectral-aware demosaicking may be based on optical flow (OF) which, for two consecutive frames $w^t$, $w^{t+1} \in W$, may be defined as $$f_V^{IP}(w^t, w^{t+1}) = \qquad (15)$$

$$\operatorname{argmin}_{v \in V_V} \min_{p \in \mathbb{R}^{n_x}, q \in \mathbb{R}^{n_y}} (\|A_I v - w^t\|^2 + \sum_{i=1}^{n_x}\sum_{j=1}^{n_y} |(A_I v)(x_i, y_j) -$$

$$w^{t+1}(x_i + p_i, y_j + q_j)|^2 + Reg_{IP}(v) + Reg_{OF}(p, q))$$

with appropriate regularisation operators $Reg_{IP}$ and $Reg_{OF}$. In other examples, extension of ( 15 ) to multiple frames may be performed.

Machine learning-based supervised or unsupervised approaches for temporally-consistent spatiospectral-aware demosaicking may be based on video super-resolution approaches. These may be based on super-resolution networks with separated or integrated motion compensation, such as optical flow estimation. Other examples may build on a recurrent neural network (RNN), such as long short-term memory (LSTM) networks, to process the video stream of temporal snapshot image data.

Similar approaches may be used to increase temporal resolution for the visualisation of data derived from snapshot mosaic imaging. In some examples, this may be done by estimating $w^{t+1/2}$ at half time steps $t+\frac{1}{2}$, i.e. doubling the frame rate for HSI data visualisation, by using the displacements p/2, q/2 as obtained during optical flow estimates, such as ( 15 ).

Parameter Estimation from Virtual Hypercubes

Based on a reconstructed virtual hypercube $v \in V_V$ parameter estimation approaches $g_P: V_V \to P^n$ can be used to estimate image property information on a pixel level over the entire active sensor area W, i.e. to estimate a property $p \in P^n := W \times \mathbb{R}^n$ of dimension $n \in \mathbb{N}$.

Approaches for spectral unmixing may be used to estimate the relative abundance of specific end-members mixed in the pixel spectra. For example, given a set of reflectances $x_{ij} \in \mathbb{R}^{n_A}$, or derived values thereof, for each pixel location $(i,j)$, $i \in \{1, \ldots, n_x\}$, $j \in \{1, \ldots, n_y\}$, of the active sensor area w the spectral mixture of $n_e \in \mathbb{N}$ end-members $\{e_k\}_{k=1}^{n_e}$ may be described by a linear spectral mixture model $$x_{ij} = \sum_{k=1}^{n_e} a_{ijk} e_k + \epsilon_{ij} \qquad (16)$$

with $\epsilon_{ij}$ denoting the random error and $a_{ijk}$ the relative abundance ratio of end-member k at pixel location (i,j). By defining the end-member matrix E: $=[e_1, \ldots, e_{n_e}] \in \mathbb{R}^{n_A \times n_e}$ and local abundances $a_{ij} := (a_{ij1}, \ldots, a_{ijn_e}) \in \mathbb{R}^{n_e}$ the model ( 16 ) can be written as $x_{ij} = E a_{ij} + \epsilon_{ij}$. With $x := (x_{ij})_{i,j} \in V_V$ and $a := (a_{ij})_{i,j} \in P^{n_e}$, an inverse problems-based approach for spectral unmixing may read $$g_P^{IP}(x) := \operatorname{argmin}_{a \in P^{n_e}} \left( \sum_{i=1}^{n_x}\sum_{j=1}^{n_y} \|E a_{ij} - x_{ij}\| + Reg_{IP}(a) \right) \qquad (17)$$

with appropriate regularisation $Reg_{IP}$ and variable constraints, such as positivity.

In one example, regularisation in ( 17 ) may be omitted which leads to a straightforward computation of the relative abundances $a \in P^{n_e}$ using normal equations.

Other choices of discrepancy measures between Ea and x in ( 17 ) may be used, such as the cosine distance. Specific assumptions on the noise level in ( 16 ) may also be made, such as the assumption that noise is independent but not identically distributed across wavelengths.

Other approaches may be based on supervised or unsupervised approaches $g_P^S V_V \to P^{n_e}$ and $g_P^U: V_V \to P^{n_e}$ similar to the demosaicking approaches ( 13 ) and ( 14 ), respectively.

Examples for spectral unmixing may include the unmixing of the end-members oxy-($HbO_2$) and deoxy-haemoglobin (Hb) per pixel with spectral characteristics of their molar extinction coefficients shown in FIG. 4. A simple model to estimate the associated relative abundance $a=g_P(x)$ may be based on absorbance estimates $x=-\ln(v)$ for a reflectance hypercube $v \in V_V$. Derived abundances $a_{HbO_2}, a_{Hb}, a_{loss} \in W$ for oxy- and deoxy-haemoglobin in addition to an end-member that accounts for scattering losses may be used to estimate total haemoglobin (or blood perfusion) $a_{HbO_2}+a_{Hb}$ and oxygenation saturation levels $a_{HbO_2}/(a_{HbO_2}+a_{Hb})$ (FIG. 10a and FIG. 10b).

Other examples for spectral unmixing may include tissue differentiation based on known spectral reflectance signatures of tissue types.

A virtual hypercube that holds the NIR reflectance information may also be used for spectral unmixing during fluorescence imaging based on known absorption and emission spectra of fluorescent compounds, such as PpIX or ICG. This may also be used for quantitative fluorescence imaging to estimate the concentration of the fluorescent compound.

Figure 10:
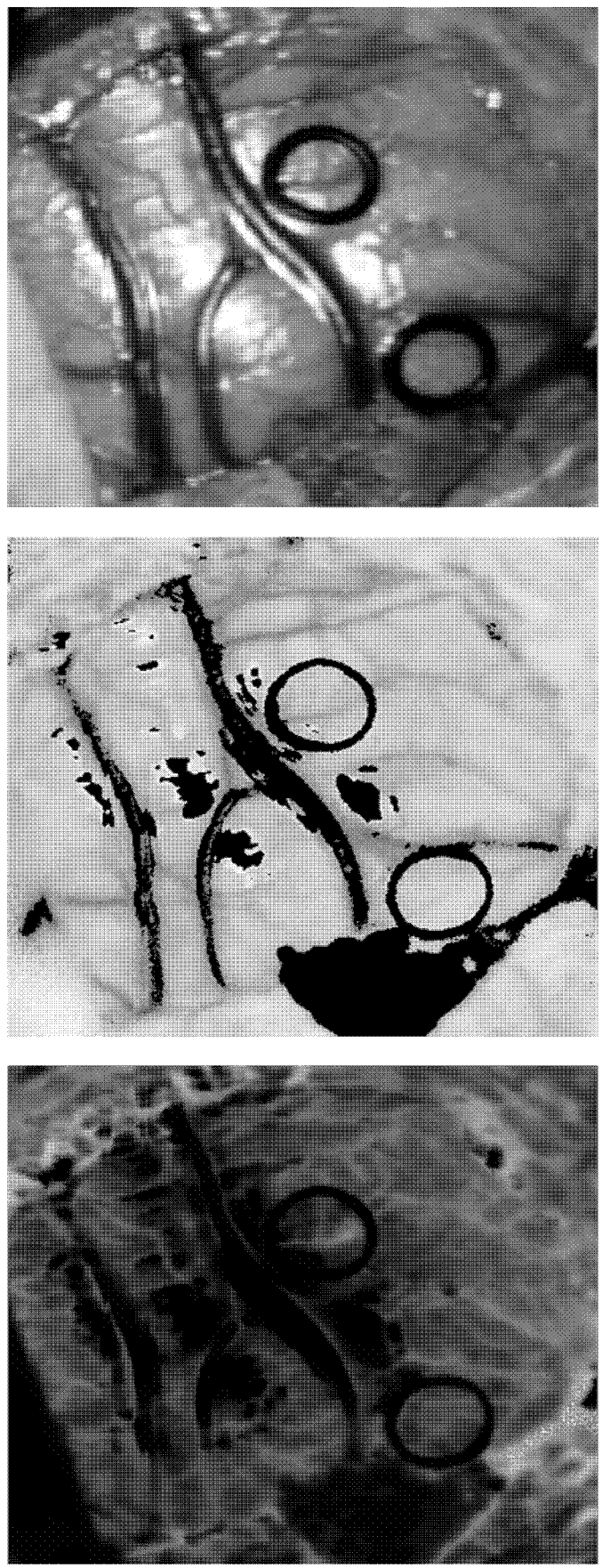
FIG. 10 is a display illustrating different tissue property parameter maps extracted from virtual hypercubes.

Pseudo-RGB images may be obtained from a virtual hypercube such as by using CIE RGB colour matching functions (FIG. 10c). If the virtual hypercube does not present spectral bands that cover the visible spectrum for RGB reconstruction, or if it covers it only partially, colorization/colour regression methods may be deployed. In case of NIR imaging in particular, this may include supervised or unsupervised methods for colorization to estimate per-pixel-RGB information. One example may include the use of cyclic adversarial networks for unpaired samples of surgical RGB images and virtual hypercube reconstructions. Other approaches may be based on the use of higher-order responses of the optical system in the visible range. In one embodiment of using NIR imaging sensors, higher-order responses, typically considered undesired spectral responses outside of the sensor's active range that need to be eliminated, could be specifically exploited to acquire spectral measurements outside of the NIR region (FIG. 3). With known filter response curves of the sensor across the optical spectrum, switching in between optical filters can be used to sequentially acquire signal either in the NIR or visible range covering RGB colour information for image reconstruction. In some examples, such a switch may advantageously be implemented through the use of a filter wheel embedded in the light source.

Other examples of parameter estimation may include the segmentation of tissues or surgical tools using data-driven supervised, semi-supervised or unsupervised/self-supervised machine learning approaches.

In other examples, a virtual hypercube and its per-pixel reflectance information may also be used to estimate optical tissue properties. An example may include the absorption coefficient which may be estimated using an approach similar, parametric model fitting to inverse adding-doubling (IAD) or inverse Monte Carlo. Based on obtained absorption estimates using, e.g., IAD, parametric model regression, supervised or semi-supervised machine learning approaches could be devised to estimate absorption maps from virtual hypercubes.

Joint segmentation and parameter estimation methods may be used. An example may include the automatic segmentation of tissue which can be used to provide a tissue-specific scattering prior to obtain more accurate absorption coefficient estimates.

Another example may include the automatic segmentation of tissue or surgical tools for more robust tissue parameter estimations. This may include accounting for image artefacts, such as specular reflections, or rejection of non-tissue-related signal contributions.

Other image analysis methods to derive information relevant for surgical decision making from a virtual hypercube may be used.

Parameter Estimation from Snapshot Imaging

As described previously, in a second embodiment parameter extractions may also be performed directly from acquired mosaic images $w \in W$ via computational approaches $f_P: W \rightarrow P^n$.

Such models may be based on the prior knowledge of 'ideal' parameter mappings $h_P: U \rightarrow P^n$.

Similar to the concept of introducing a spectral correction operator $I \otimes C: V_F \rightarrow V_V$ between band-filtered and virtual hypercube spaces, a mapping $\pi(\cdot; \theta): V_F \rightarrow P^n$ with model parameters $\theta$ can be established such that $\pi \cdot (I \otimes B_F) \approx h_P$. Such mapping may be determined via $$\theta^* := \mathrm{argmin}_\theta(\|\pi(\cdot;\theta) \cdot (I \otimes B_F) - h_P\| + \mathrm{Reg}(\theta)) \quad (18)$$

with appropriate regularisation Reg and variable constraints, such as positivity. With (11), i.e.

$$v_F^* = \mathrm{argmin}_{v \in V_F}(\|T \cdot S)v - w\| \mathrm{Reg}(v)) \quad (19)$$

with appropriate regularisation term such as of the form $\mathrm{Reg}(\pi(v;\theta^*))$, this leads to $$f_P(w) = \pi(v^*_F; \theta^*). \quad (20)$$

In other examples, the pseudo-inverse $\pi^\dagger(\cdot;\theta): P^n \rightarrow V_F$ with model parameters $\theta$ may be determined via $$\min_\theta (\|\pi^\dagger(\cdot; \theta) \circ h_P - I \otimes B_F\| + \mathrm{Reg}(\theta)) \quad (21)$$

with appropriate regularisation Reg and variable constraints, such as positivity. The forward model can then be defined as $$A_P := T \cdot S \cdot \pi^\dagger : P^n \rightarrow W. \quad (22)$$

Similar to above mentioned examples (10)-(14), inverse problems-based approaches, supervised, semi-supervised and unsupervised approaches may be used to estimate the parameter mapping $f_P: W \rightarrow P^n$.

It shall be noted that instead of estimating $\pi$ or $\pi^\dagger$, invertible models may be used, such as invertible neural networks, which not only learn a forward mapping but also to establish the corresponding inverse simultaneously.

As one example, $h_P$ can be derived from the spectral unmixing model used to estimate abundance for oxy- and deoxy-haemoglobin. By extending the linear spectral mixture model (16) from the space $\mathbb{R}^{n_A}$ to $\mathbb{R}^{n_A}$, normal equations lead to the explicit formulation of $$h_P(u) = -(I \otimes (E^T E)^{-1} E^T)(\ln(u)) \in P^3 \quad (23)$$

whereby $E \in \mathbb{R}^{n_A \times 3}$.

In other examples pseudo-RGB images may be obtained from snapshot images using data-driven machine learning approaches. One example may include the use of cyclic adversarial networks for unpaired samples of surgical RGB and snapshot mosaic images.

Uncertainty Estimates

Whereas presented forward models are typically well-defined, the problem of estimating the inverse is generally ambiguous, such as the pixel-wise reconstruction $f_P: W \rightarrow P^n$ of tissue property parameters from low-resolution snapshot image acquisitions. It shall be obvious that for all presented computational approaches, additional uncertainty quantification capabilities may be introduced to estimate the uncertainty of obtained outcomes. This may include approaches such as dropout sampling, probabilistic inference, ensembles of estimators, or test-time augmentations.

In other embodiments, invertible mappings may be used in the presented models such as obtained by invertible neural networks, which not only learn a forward mapping but also establish the corresponding inverse process. Such approaches may also be used to recover the full posterior distribution able to capture uncertainty in obtained solution estimates.

Uncertainty estimates may be displayed to the user or may be used as part of a computational pipeline or visualisation strategy. According to one example, uncertainty estimates relating to parameter estimates may be used to choose and display only the estimates meeting a given certainty criteria such as a threshold.

Detailed Description of Embodiments Relating to an iHSI System

We first present exemplar embodiments of a system according to the invention that integrates two state-of-the-art industrial HSI cameras as part of an iHSI system setup. Both iHSI embodiments are then evaluated and scored against the presented design requirements (Table 1 and Table 2). Following this, we perform a controlled checkerboard experiment to demonstrate that reliable reflectance measurements can be obtained with these embodiments using both HSI cameras. An ex vivo experiment demonstrates the reflectance properties for a range of tissue types. In this embodiment, a standard tripod system used for photography advantageously allows for versatile imaging configurations in a controlled environment. Finally, we describe a successful ethically-approved in-patient clinical feasibility case study that demonstrates the ability of a real-time iHSI embodiment to seamlessly integrate into the surgical workflow while respecting clinical requirements in the OR such as sterility.

HSI System Embodiments.

Two hyperspectral imaging cameras were investigated as part of embodying the proposed iHSI invention (Table 3): (i) a linescan HSI embodiment using the Imec snapscan VNIR, i.e. visible (VIS) to near-infrared (NIR) region, camera and (ii) a snapshot HSI embodiment using the Photonfocus MV0-D2048×1088-C01-HS02-160-G2 camera.

The linescan embodiment captures hypercube images with a spatial resolution of up to 3650×2048 pixels for 150+ spectral bands between 470 nm to 900 nm. The imaging speed to acquire a full hypercube ranges between 2 s and 40 s depending on acquisition parameters, illumination and imaging target. The camera without optics has a size of 10×7×6.5 cm3 and a weight of 0.58 kg. The linescan technology is characterised with high SNRs across the spectral range. An integrated shutter automatically measures dark currents therefore requiring only the manual acquisition of a white reference image for image calibration.

The Photonfocus camera deploys the Imec snapshot mosaic CMV2K-SM5×5-NIR sensor which acquires 25 spectral bands in a 5×5 mosaic between the spectral range of 665 nm and 975 nm. With a sensor resolution of 2048×1088 pixels, hyperspectral data is acquired with a spatial resolution of 409×217 pixels per spectral band. Video-rate imaging of snapshot data is achieved with a speed of up to 50 FPS depending on acquisition parameters. The camera without optics has a size of 3×3×5.4 $cm^3$ and a weight of 0.08 kg.

Figure 12:
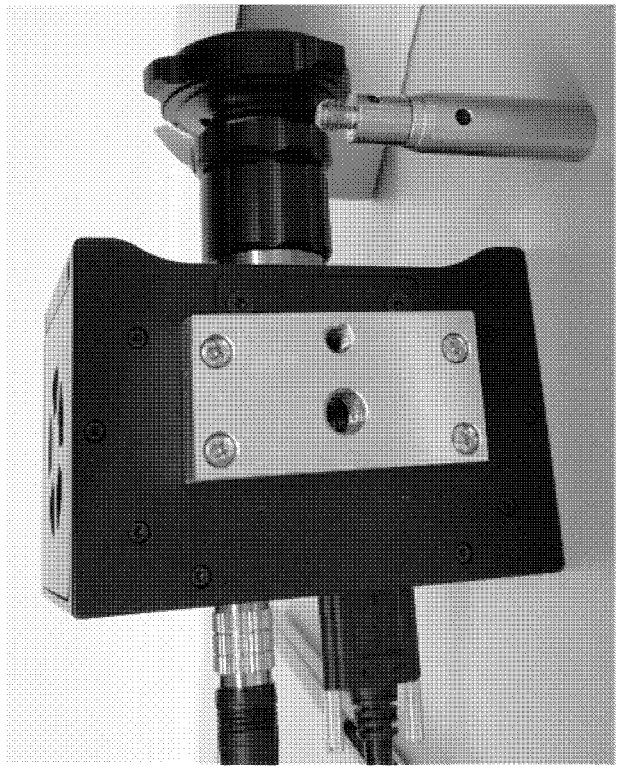
FIG. 12 is a schematic diagram of a linescan and snapscan imaging embodiment.
Figure 12:
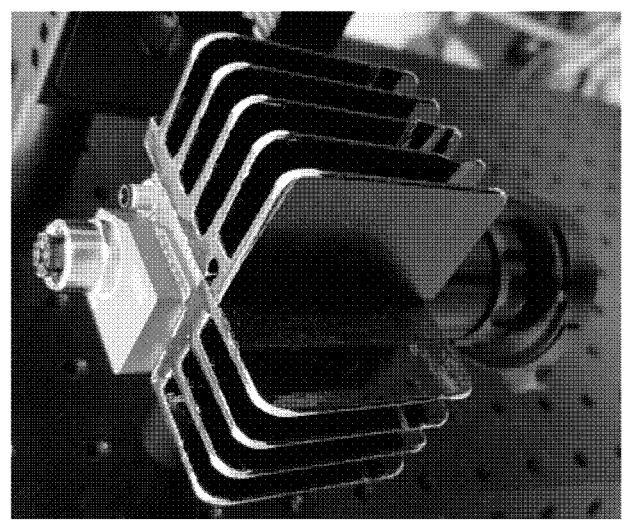

A passive prototype cooling system was fabricated with rounded edges and installed by mounting two heat sinks on the sides of the camera to keep operating temperatures, and therefore imaging noise, low during image acquisition (FIG. 12a). This increased the overall dimensions by about 3 cm in each direction with additional weight of about 0.2 kg.

An Asahi Spectra MAX-350 light source (300 W Xenon lamp) was used to provide broadband light. Depending on the experiment either a VIS module or UV-NIR mirror module was available which provided light over a 385-740 nm or 250-1050 nm region, respectively. In case of using the UV-NIR mirror module an additional 400 nm longpass filter (Asahi Spectra XUL0400) was placed in front of the mirror module to suppress ultraviolet (UV) light to improve the light safety profile. For the Photonfocus camera, a 670 nm longpass filter (Asahi Spectra XVL0670) was placed in the filter wheel to avoid signal contamination due to out-of-band sensor responses during image acquisition originating from sensor sensitivity to light in the VIS spectrum. Light intensity can be adjusted on the Asahi Light source between 5% and 100% using integer increments. The light source is connected via a Karl Storz fiber optic light cable 495NCS to a Karl Storz 0° VITOM surgical exoscope 20916025AA which allows imaging at a safe distance between 25 cm to 75 cm. A custom adapter was used to plug the light guide in the Asahi light source. The exoscope attaches to the respective HSI camera via individual RVA Synergies C-Mount 18-35 mm ZOOM Endoscope Couplers which additionally provide a manual zooming and focusing mechanism.

For calibration during all experiments, a 95% reflectance tile was used to acquire a white reference image. For the Photonfocus camera, a separate dark reference image was acquired with a cap to close the lens.

Verification of iHSI Embodiments Against Design Specifications.

Both the linescan and snapshot camera-based iHSI embodiments were assessed towards the suitability for an intraoperative setup against the design requirements as specified in Table 2. A summary of the assessment is provided in Table 3.

Figure 13:
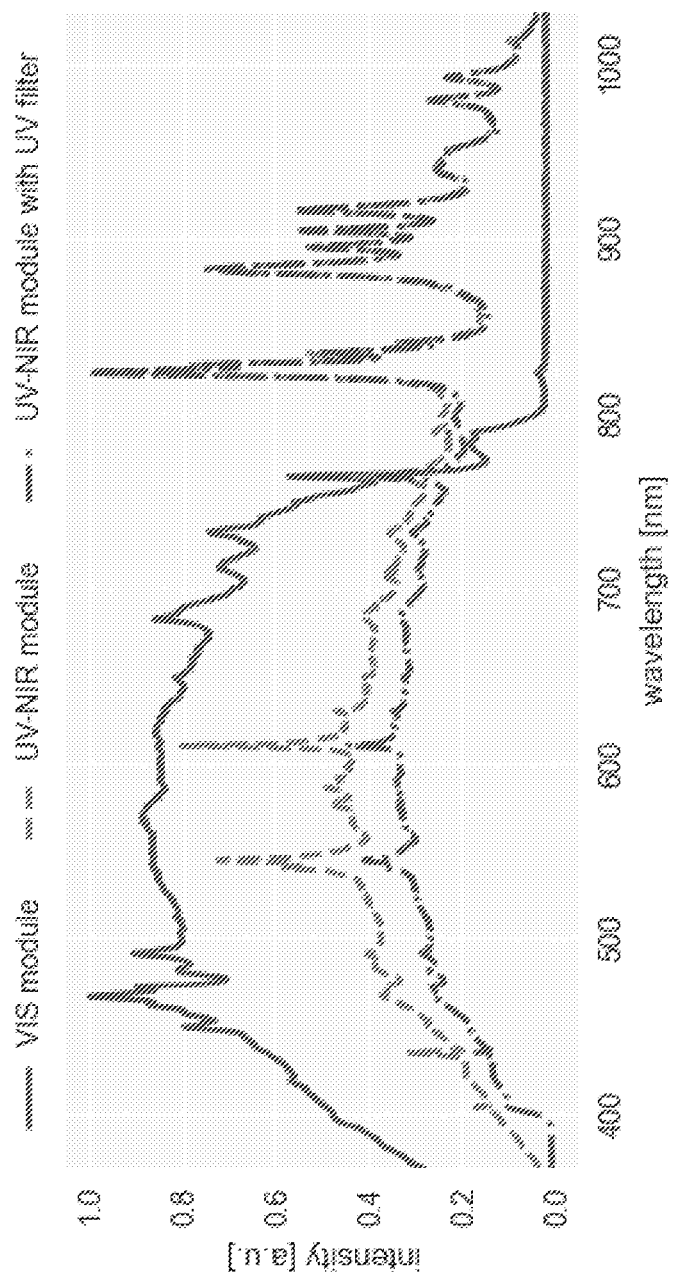
FIG. 13 is a schematic diagram of a Xenon light source with and without UV filter.

Starting with the system requirements, sterility for both camera setups can be ensured using a combination of drapes and sterile components (T2). However, it is apparent from the respective camera specifications that the snapshot camera allows for a more compact iHSI system given its smaller camera dimensions and weight (T2, T3). The Xenon light source provides sufficient energy across VIS and NIR spectral ranges using the UV-NIR mirror module (T7) (250-1050 nm) as shown in FIG. 13.

Light safety is advantageously ensured by blocking UV light using a 400 nm longpass filter (T8). The light source permits remote configuration using a serial communication protocol allowing for adjustment of filter wheel position and light intensity using customized software (T10). Similarly, both linescan and snapshot camera systems come with API interfaces to allow for remote control and software integration.

Device handling is critical to ensure camera systems can be mounted and moved securely during surgery without adversely impacting the surgical workflow and sterility (T2, T3, T9, T10). Due to the compactness of the snapshot camera-based system, this can be easily achieved using a mechanical arm construction (T9).

However, for the linescan camera-based system, weight and form factor do not allow using the same approach. Mounting and pivoting in rotated positions of the camera system with weight supported only by the endoscope adapter and mechanical arm were not considered safe.

Both camera setups rely on the same optical setup and adapters and allow for imaging at a safe distance to the surgical cavity between 250 mm and 750 mm (T12). When using a fixed circular 50 mm FOV at a working distance of 250 mm both systems have a depth of field of 35 mm (T12-14) based on the exoscope manufacturer's specification [33]. Using the endoscope adapter, manual focus and zoom adjustments can be made to provide sharp imaging at a given focal distance (T11). In terms of HSI data quality, both spatial and spectral image resolution of the linescan camera is far superior than the snapshot camera (T15, T17). In particular, in addition to the fewer spectral bands sampled by the snapshot camera, additional postprocessing methods such as demosaicking, are needed to account for the sparse spatial sampling to obtain HSI data information on a sufficiently high spatial resolution for tissue analysis larger than 409×217 pixels per spectral band (T15, T17). While the linescan system covers a wide spectral range in both the VIS and NIR region to allow for rich feature extraction, the snapshot camera only provides NIR spectral information. Furthermore, the linescan technology comes with high-fidelity HSI signal measurement with high signal-to-noise ratios. In contrast, signals acquired using snapshot imaging are characterized by multimodal spectral band and crosstalk signal contamination resulting from the mosaic imaging sensor which needs to be accounted for. Consequently, the linescan system could potentially extract a wider range of relevant surgical features. However, the acquisition speed of the linescan camera between 2 s and 40 s per image can interrupt the surgical workflow without providing video-rate information needed for real-time surgical guidance (T19). In particular, it is prone to motion artefacts if non-static imaging targets are imaged. In contrast, high frame rates of up to 50 FPS for the snapshot camera allow for real-time visualisation that can easily capture moving imaging targets (T19). For the linescan camera, image calibration can be achieved by acquiring a white reference image only due to its integrated shutter. For the snapshot camera, both a dark and white reference image needs to be acquired T18. For both camera setups, a robust calibration approach that can deal with changing illumination and imaging scenes is crucial to estimate reliable HSI information for intraoperative surgical guidance.

Overall, the linescan camera imaging quality was superior to the one provided by the snapshot camera in these embodiments. However, given its form factor, a more elaborate mounting mechanism would advantageously ensure safe and sterile handling of the camera during surgery. Moreover, its comparatively low imaging rate does not allow for HSI data capture without interrupting the surgical workflow which is crucial to provide real-time information for seamless surgical guidance. Nevertheless, its imaging characteristics can ensure high-quality HSI in controlled set ups. In contrast, the video-rate snapshot camera allows for a compact and sterile iHSI system that can be integrated into surgical workflows using standard clinical mechanical arm constructions. For reliable tissue analysis, image processing methods can advantageously account for the reduced spatial and spectral image resolution in addition to lower signal quality that are characteristic for mosaic snapshot sensors.

Checkerboard Study: iHSI System Embodiment Verification.

Both the linescan and snapshot camera were tested in combination with the proposed intraoperative optical system embodiments, i.e. the endoscope adapter and exoscope, to acquire HSI data in a controlled experiment using a datacolor SpyderCHECKR checkerboard which comes with 48 colour patches. For the experiments, the Asahi light source was used with the UV-NIR module in combination with the 400 nm longpass filter to provide light for 400-1050 nm. Reference spectra were acquired using an Ocean Optics Maya 2000 Pro 200-1100 nm spectrometer with an Ocean Optics QR600-7-VIS125BX reflectance probe (FIG. 4).

For the linescan camera, images were acquired using an exposure time of 10 ms and gain of 1.2. For the snapshot camera, images were acquired using an exposure time of 15 ms, gain of 2. Proprietary software was used to provide spectrally calibrated hypercube reflectance data for image analysis for both camera systems using the default image calibration files provided with the cameras. In particular, no dedicated system-wide calibration was performed to account for the specific light source intensity spectrum (FIG. 13) and individual optical components of the iHSI system—such as optical filters, endoscope adapter and exoscope—during image calibration.

Figure 14:
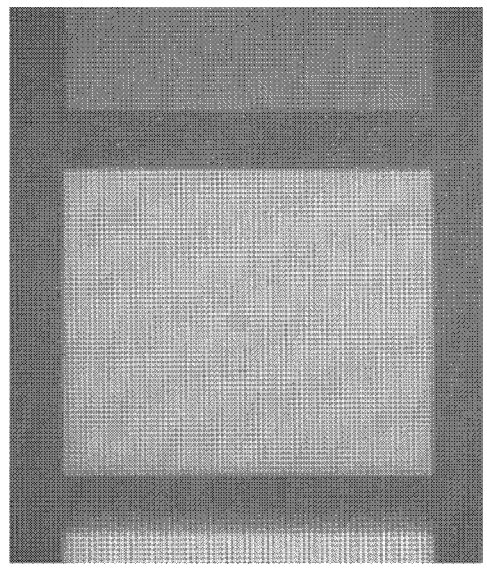
FIG. 14 is a display of a checkerboard experiment setup.
Figure 14:
Figure 14:
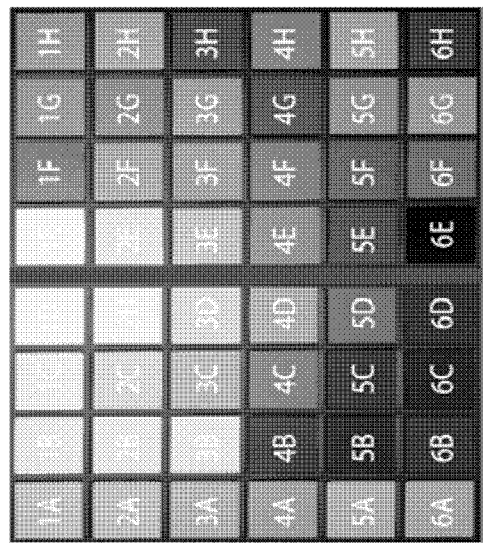

Both linescan and snapshot cameras were placed at a 35 cm distance to the checkerboard whereby images were acquired for each patch individually. For each calibrated hypercube image, five circular regions of 10 pixel radius, distributed over the colour patch, were manually segmented for spectral analysis (FIG. 14c).

Figure 15:
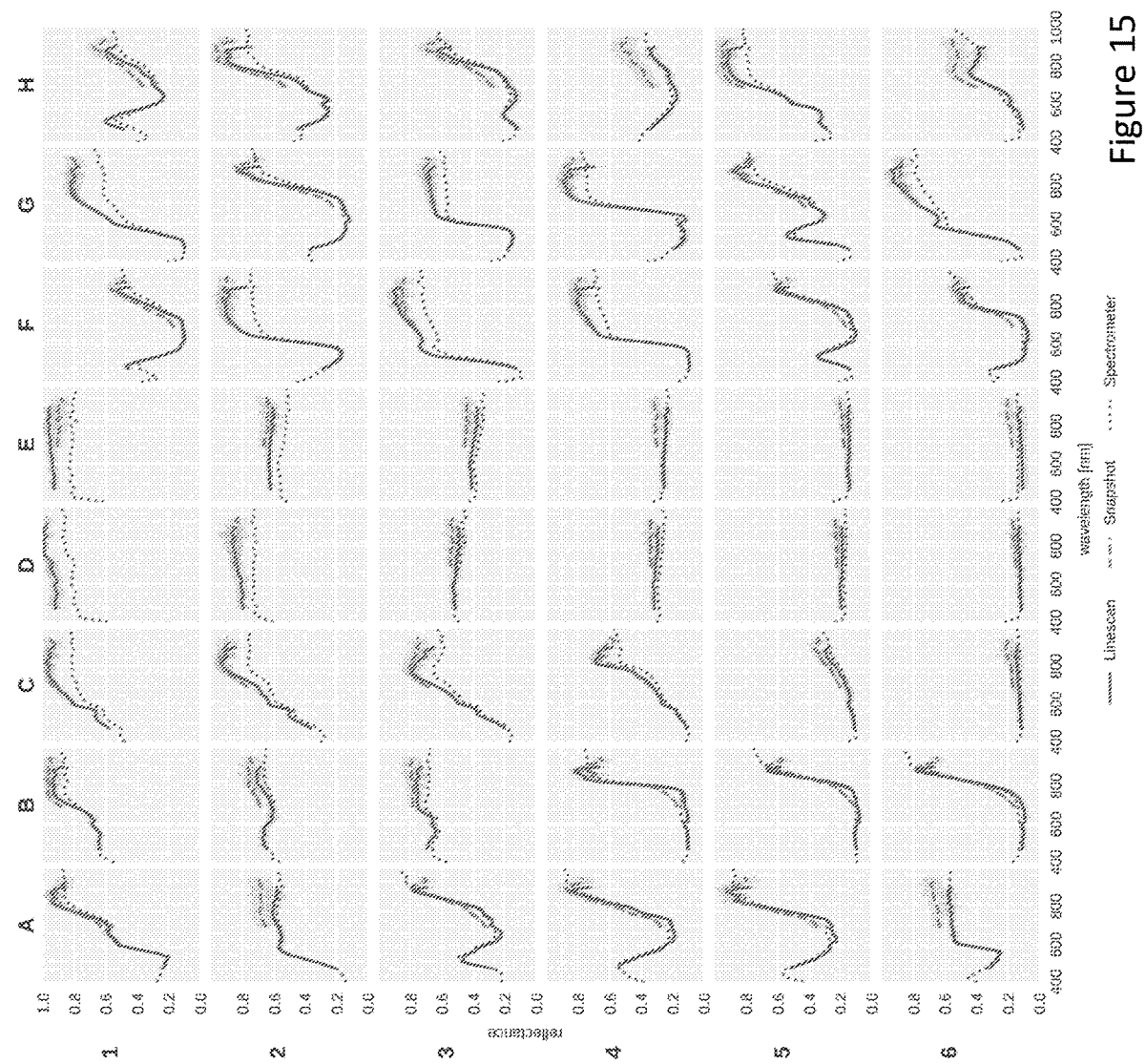
FIG. 15 is a graph showing example reconstructions of a checkerboard experiment.

FIG. 15 provides a comparison between the reference data and spectral information obtained by the iHSI systems using the linescan and snapshot cameras. It can be seen that estimated reflectances for both linescan and snapshot iHSI systems largely follow the spectrometer reference measurements.

Ex Vivo Study: Cadaveric Veal Experiment.

An ex vivo experiment using a fresh bovine calf cadaver was performed in a controlled environment to investigate tissue properties with the iHSI embodiments for both linescan and snapshot cameras, performed at Balgrist University Hospital, Zurich, Switzerland. A bovine calf cadaver was selected because its anatomy approximates that of the human spine [36].

Figure 16:
FIG. 16 is a display of an ex vivo experiment setup.

Various tissue types were exposed for tissue analysis including tendons, muscle, bone, joint capsule, dura and spinal cord. To achieve optimal orientation and position for imaging cadaveric tissue samples, a standard tripod system was advantageously used for mounting the iHSI camera systems (FIG. 16). For both linescan and snapshot cameras, secure attachment was achieved using custom adapter plates with ¼-20 UNC and ⅜-16 UNC threaded holes (FIG. 12b). An additional Thorlabs DCC3260C RGB camera was used for the experiment to provide high-resolution 1936×1216 RGB imaging. The camera without optics has a size of 2.9×3.5×4.4 cm$^3$ and a weight of 0.04 kg. Given its C-mount camera lens mount, it could be used with the same endoscope adapter as part of the same iHSI setup. Additionally, its housing comes with a ¼-20 UNC threaded hole suitable for attaching quick release tripod plates.

Figure 17:
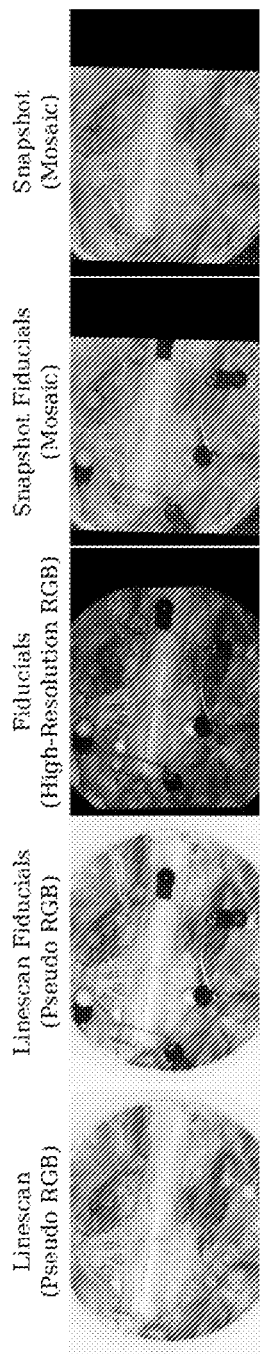
FIG. 17 is a display of example sequence of camera acquisitions during ex vivo imaging to capture HSI data of the spinal cord and rootlets.

Imaging of the exposed tissue using the three cameras followed the scheme as summarized in FIG. 17. By using separate fiducials which are visible and differentiable across the VIS and NIR spectrum it was ensured that images acquired with different cameras could be put in alignment retrospectively. We used a set of six pinheads with colours red, black, blue, white, green and yellow tied together with a nylon thread for facilitated handling during the experiment. After positioning the first HSI camera (either linescan or snapshot camera) and adjusting zoom and focus for imaging the tissue sample, fiducials were placed on the tissue to ensure they are within the FOV. Fiducials were then removed from the scene for image capture and carefully placed back to avoid anatomical changes before acquiring a second image with the same HSI camera. Without touching the scene, the HSI camera was swapped with the RGB camera using the tripod quick release mechanism to acquire an RGB image of the tissue sample with fiducials. Subsequently, without making changes to the scene, the RGB camera was swapped with the second HSI camera on the tripod. Minor adjustments to camera position, zoom and focus were typically needed to ensure the target tissue was in focus and the fiducials within the FOV before an image was acquired. After careful removal of the fiducials, another image was acquired of the same scene without making any other changes to the setup. For spectral analysis, a neurosurgeon manually annotated relevant tissue types in the pseudo RGB linescan image, which was obtained by assigning the channels red, green and blue to the wavelengths of 660 nm, 570 nm and 500 nm, respectively. By manually annotating the circular fiducials, alignment between all images was achieved using affine point-based registration [37]. Manual segmentations in the linescan image space were then propagated to the snapshot image space for analysis using the obtained point-based affine registration.

During the ex vivo experiment, only the VIS mirror module was available for the light source therefore providing light between 385 nm and 740 nm. For NIR imaging with the snapshot camera, an additional 670 nm longpass optical filter in the filter wheel of the light source was activated. A gain of 3.01 and exposure time of 20 ms were used for the snapshot camera for all scenes whereby video imaging was performed to acquire multiple images of each individual static scene. On average, this led to the acquisition of 18 snapshot mosaic images per scene whose mean image was used for spectral analysis. For the linescan camera, a gain of 2 and exposure time of 20 ms were used. Light intensities were set to 100%, 100% and 50% for the snapshot, linescan and high-resolution RGB cameras, respectively. Imaging for all cameras was performed with room lights switched off and window blinds down to reduce the impact of background light. To ease the imaging workflow, acquisition of reference data for image calibration was performed once for both linescan and snapshot cameras in the beginning and the end of the experiment, respectively. Therefore, the same white balancing information for each HSI camera was used for data calibration of all imagery associated with different anatomical locations.

Figure 18:
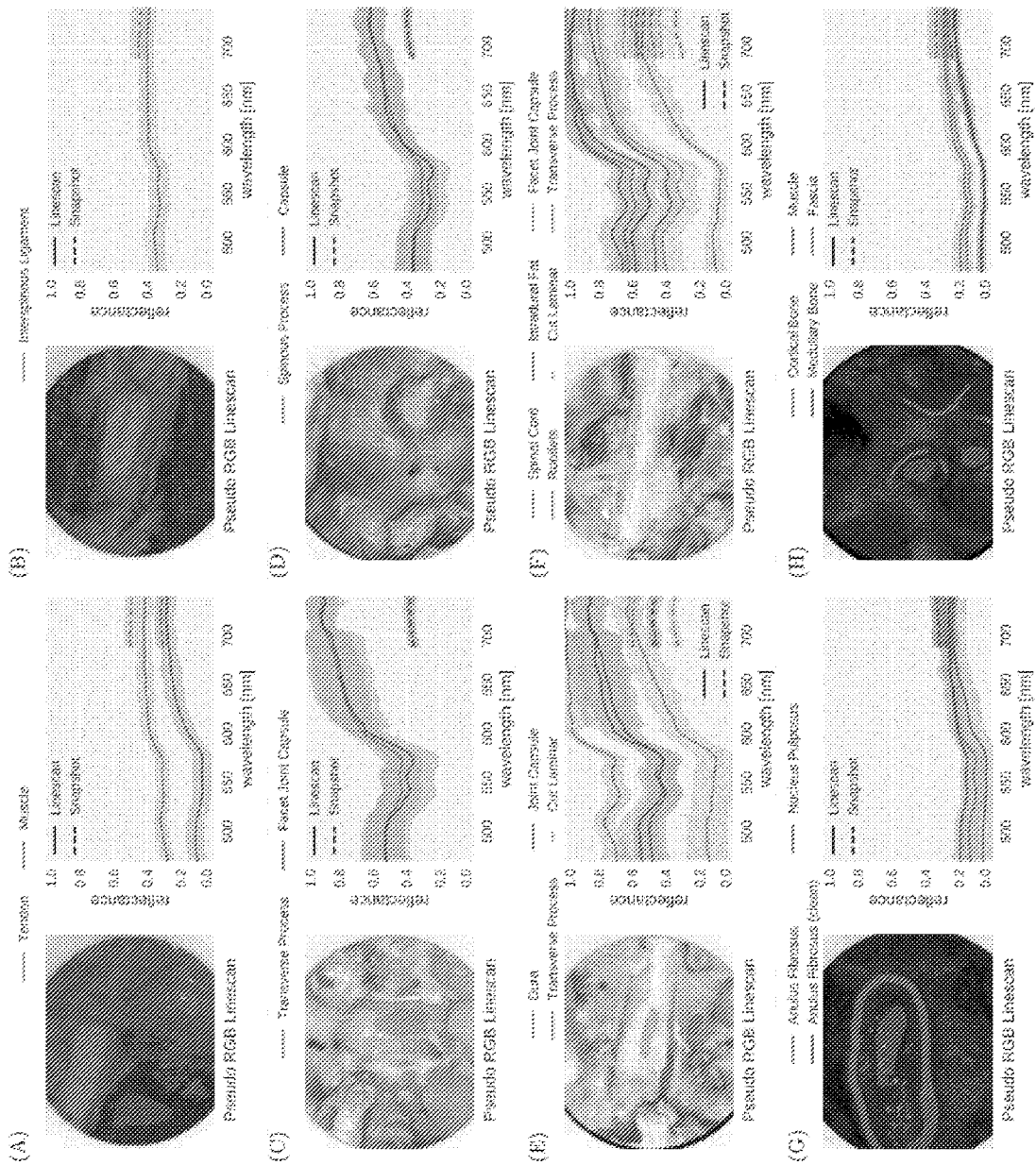
FIG. 18 is a display of a comparison of estimated reflectance curves.

FIG. 18 provides a comparison of estimated reflectance curves between 470 nm and 740 nm of both linescan and snapshot-based iHSI systems for eight different anatomical scenes, referenced in FIG. 16b. For the snapshot camera, only 5 out of 23 reconstructed bands were available for analysing the measurements between 670 nm and 740 nm. In general, relative distribution and qualitative behaviour of reflectance values across tissue types for overlapping spectral bands between the cameras are well aligned.

In Patient Clinical Feasibility Case Study: Spinal Fusion Surgery.

Following the assessment of the proposed iHSI embodiments for both linescan and snapshot cameras against design requirements critical for surgery in combination with the quantitative and qualitative assessments, the snapshot-based embodiment would advantageously provide real-time HSI that can seamlessly integrate into the surgical workflow. To confirm this hypothesis, we conducted an intraoperative clinical feasibility case study as part of a spinal fusion surgery at Balgrist University Hospital, Zurich, Switzerland. The study was approved by the cantonal ethical committee (BASEC Nr: req-2019-00939).

FIG. 5 presents a schematic of the iHSI embodiment deployed in surgery. In addition to the system components described previously a standard Karl Storz mechanical arm was used for safe attachment of the iHSI camera system to the surgical table using an articulated L-shaped stand (28272HC) via a clamping jaw (28272UGK). Safe attachment to the snapshot HSI camera via the VITOM exoscope was achieved via an appropriate rotation socket (28172HR) and a clamping cylinder (28272CN). Overall sterility of the system was ensured by autoclaving the mechanical arm, the exoscope and the light guide before surgery and draping the camera and associated cable.

Figure 19:
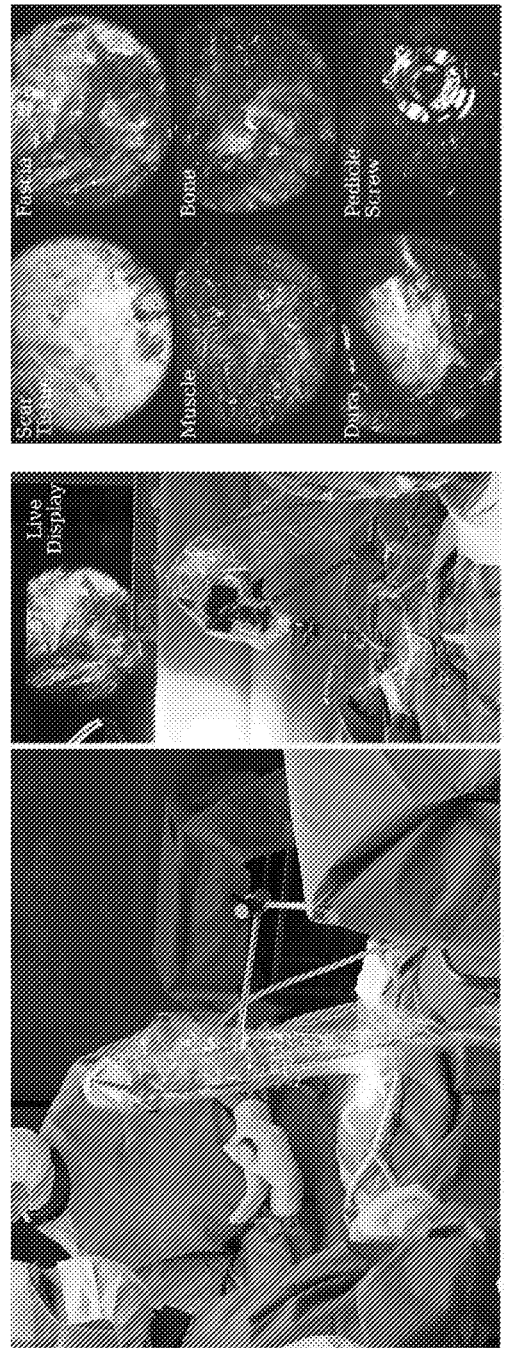
FIG. 19 is a display of the intraoperative HSI setup (iHSI) during spinal fusion study with example in vivo snapshot mosaic images.

The primary goal of the intraoperative clinical feasibility case study was to confirm the system's integration into the standard surgical workflow. To focus on this objective, we chose to mimic current optical camera systems during surgery and used white light between 385 nm and 740 nm without the 670 nm longpass filter. For the snapshot camera, a gain of 4 and exposure time of 20 ms was chosen with the light source providing 100% of light intensity. A laptop running customized software for real-time interaction with the camera system and data visualisation was placed onto a trolley at a safe distance outside of the sterile environment. Connection to a monitor in the OR provided a live display of captured video-rate HSI data (FIG. 19a). In particular, this allowed for instant feedback to and interaction with the surgical team for adjusting camera position and orientation in addition to endoscope adapter settings to acquire in-focus data for the region of surgical interest. Using this setup, in vivo imaging was performed at eight different stages during surgery to acquire HSI data of various tissue types including skin, adipose tissue, scar tissue, fascia, muscle, bone, pedicle screws and dura (FIG. 19b). Imaging of each anatomy lasted between 6 s and 44 s with minimal disruption to the surgical workflow. After successful surgery with seamless transitions to acquire HSI data, a final recording of 3 min 16 s was performed to capture imaging data covering the surgical cavity.

DISCUSSION AND CONCLUSION

Previous work has underlined the potential of HSI for intraoperative tissue characterisation as a non-contact, non-ionising, non-invasive and label-free imaging modality. Despite numerous research studies exploring the clinical potential of HSI for surgery, to our knowledge, no HSI system has been presented which follows strict clinical requirements including sterility and seamless integration into the surgical workflow that can provide real-time information for intraoperative surgical guidance.

Here we presented an embodiment of an HSI system for intraoperative surgical guidance suitable for open surgery. However, our invention allows for adaptation for endoscopic and microscopic surgery. We embodied our invention in two state-of-the-art industrial HSI camera systems, based on either linescan or snapshot technology, and assessed their suitability for surgical use. Based on our established criteria, we presented an intraoperative HSI embodiment and perform a scoring against these requirements by considering both HSI cameras. We performed controlled checkerboard experiments demonstrating that reliable reflectance measurements can be obtained with the proposed embodiments using both HSI cameras. Ex vivo experiments were performed to investigate reflectance properties for a range of tissue types including tendons, muscle, bone, joint capsule, dura and spinal cord with both iHSI camera setups mounted on a standard tripod system allowing for versatile imaging configurations in a controlled environment. In particular, this proved to be a suitable setup for the linescan camera to provide high-resolution data in both spatial and spectral dimensions across the VIS and NIR spectrum for ex vivo tissue analysis. The iHSI system allowed for seamless and safe transitions during various stages of spinal fusion surgery and acquired video-rate HSI data of multiple tissue types including skin, adipose tissue, fascia, muscle, bone, pedicle screws and dura. Our successful clinical feasibility case study demonstrated that the proposed iHSI system seamlessly integrates into the surgical workflow by respecting critical clinical requirements such as sterility and is capable of providing wide-field video-rate HSI imagery. By developing a data-driven information processing pipeline such video-rate HSI data can be utilised to provide real-time wide-field tissue characterisation for intraoperative surgical guidance.

The proposed ex vivo setup can be used for combined experiments to acquire both high-resolution linescan and low-resolution snapshot HSI data. This can advantageously provide crucial information for developing real-time demosaicking and tissue differentiation methods for snapshot HSI.

As part of the exemplar embodiments, any compact camera that follows camera dimension and weight requirements as outlined in Table 1 can be integrated into the proposed iHSI system setup in a straightforward manner. It can also be beneficial to enable HSI acquisition with a variable working distance, field of view, depth of field and depth of focus (Table 2) which in turn would enable the device to be integrated with various commercial exoscopic surgical systems [34] and would ensure parity with current microscopic standards [38].

Our in vivo clinical feasibility case study demonstrated that embodiments of our invention integrate well into a standard surgical workflow and are capable of capturing HSI data. Overall, members of the surgical and theatre team found the tested embodiment straightforward to use although routine training will need to be implemented to ensure smooth operating during surgery. The tested embodiment posed no safety concerns to team members and the system's size, weight and portability were acceptable in maintaining a smooth surgical workflow.

TABLE 1

Overview of advantageous functional design requirements of a hyperspectral imaging system embodiment for intraoperative surgical guidance. Corresponding advantageous technical requirements from Table 2 are listed in the rightmost column.

| | Advantageous Minimum Requirement | Target Advantageous Requirement | Req |
|---|---|---|---|
| | — | — | — |
| F1. Surgical safety and sterility | Safe and sterile intraoperative use should advantageously be possible throughout the surgical procedure. | Ibid. | T1, T2, T8, T9, T12 |
| F2. Technical safety | Device should advantageously comply with electrical and light source safety standards so that it may be used safely within the operating theatre without causing tissue injury. | Ibid. | T1, T2, T4-6, T8, T9, T16 |
| F3. Lighting | Light and illumination requirements should advantageously not impede surgical workflow. | Ibid. Additionally, light and illumination it should advantageously be possible to adjust to accommodate the surgeon's needs. | T7, T10, T18 |
| F4. Maintenance | Maintenance and cleaning requirements should advantageously comply with standard clinical practice. | Ibid. | T1, T2 |
| F5. Device handling | Device should advantageously be securely held or mounted during the procedure but easily manoeuvrable. | Handheld device should advantageously be easily manoeuvrable and be light enough to position securely without the need for an assistant. | T2-6, T10, T12 |
| F6. Anatomical coverage | Field of view (FOV) and depth of imaging should advantageously provide information compatible with the surgical action. | Ibid. Additional monitoring capabilities should advantageously be available. | T11-13, T19 |
| F7. Anatomical feature | Critical functional or semantic features to increase surgical precision and patient safety during the procedure. | Multiple functional and semantic features to increase surgical precision and patient safety for comprehensive patient monitoring. | T7, T11 and T13-19 |
| F8. Anatomical detail | Resolution suitable to spatially identify/differentiate tissue within the surgical field. | Resolution suitable to spatially identify/differentiate anatomical tissue with high anatomical detail. | T11 and T13-17 |
| F9. Imaging rate | Video-rate imaging for instant surgeon feedback and seamless workflow integration. | Fast video-rate imaging for instant and smooth surgeon feedback and seamless workflow integration. | T19 |
| F10. Visualisation | Accurate visualisation of extracted information for surgical guidance. | Intuitive and accurate visualisation of extracted information for seamless surgical guidance. | T7 and T15-18 |

TABLE 2

Overview of advantageous technical requirements of a hyperspectral imaging system embodiment for intraoperative surgical guidance. Corresponding advantageous functional requirements from Table 1 are listed in the rightmost column.

| | Advantageous Minimum Requirement | Target Advantageous Requirement | Req |
|---|---|---|---|
| T1. System maintenance | System components may advantageously be suitable for cleaning using a universal antimicrobial surface wipe. | Ibid. Additional camera housing resistance advantageously protects against dust and splashing liquids. | F1, F2, F4 |
| T2. Camera dimensions | Smaller than 10 × 10 × 12 cm$^3$. | Smaller than 6 × 6 × 8 cm$^3$. | F1, F2, F4, F5 |
| T3. Camera weight | Lighter than 1 kg. | Lighter than 0.5 kg. | F5 |
| T4. Camera edges | No sharp edges of camera housing. | Ibid. | F2, F5 |
| T5. Camera temperature | Temperature lower than 40° C. | Ibid. | F2, F5 |
| T6. Camera connectivity | No more than two cables to provide power and fast data link | One cable to provide both power and fast data connection. | F2, F5 |
| T7. Light source energy | Adequate uniform coverage of required spectral range (cf. T16). | Ibid. | F2, F3, F7, F10 |
| T8. Light source safety | Adherence to MPE limits with ionizing UV wavelengths (<400 nm) eliminated. | Ibid. | F1, F2, F7, F10 |
| T9. System mount | Static system mount possible. | Adjustable system mount possible. | F1, F2 |
| T10. Camera settings | Manual adjustments of camera acquisition settings. | Automatic adjustments to obtain ideal camera acquisition settings. | F5, F6 |
| T11. Focus | Manual focus of target tissue. | Autofocus of target tissue. | F6-8 |
| T12. Working distance | Fixed WD between 200 mm and 300 mm. | Variable WD between 200 mm and 750 mm. | F1, F3 and F5-6 |
| T13. Field of View | Fixed FOV between 40 mm and 60 mm. | Variable FOV between 40 mm and 150 mm. | F6-8 |
| T14. Depth of Field | At least 20 mm DOF for 50 mm FOV at fixed WD of 250 mm. | Variable 15 mm to 100 mm DOF. | F6-8 |
| T15. Spectral bands | At least 16 spectral bands. | At least 100 spectral bands for fine spectral sampling. | F2, F7, F8, F10 |
| T16. Spectral range | At least a spectral coverage of 160 nm. | At least a spectral coverage of 500 nm. | F2, F7, F8, F10 and T7 |
| T17. Spatial image definition | 1920 × 1080 pixels. | 3840 × 2160 pixels. | F6-8, F10 |
| T18. Image calibration | Satisfactory image calibration to enable reliable feature extraction during surgery. | Seamless and on-the-fly calibration possible for reliable feature extraction depending on surgical requirements and light conditions. | F3, F7, F10 |
| T19. Imaging rate | Video-rate imaging of at least 7 FPS. | Video-rate imaging of at least 30 FPS. | F6, F7, F9 |

TABLE 3

Verification of intraoperative hyperspectral imaging embodiments based on whether advantageous requirements as outlined in Table 2 are met. Assessment is performed for two camera setups with ratings (R) of 0 (advantageous minimum requirement not met), 1 (advantageous minimum requirement met) and 2 (target advantageous requirement met) using the exemplar embodiments described in the text.

| | Linescan camera based embodiment | R | Snapshot camera based embodiment | R |
|---|---|---|---|---|
| T1 Camera maintenance | All components may be effectively cleaned using a universal surface wipe. | 1 | Ibid. | 1 |
| T2 Camera Dimensions | 10 × 7 × 6.5 cm$^3$. | 1 | 6 × 6 × 5.4 cm$^3$ (incl. heat sinks). | 2 |
| T3 Camera Weight | 0.58 kg. | 1 | 0.28 kg (incl. heat sinks). | 2 |
| T4 Camera edges | Camera housing with smooth edges. | 2 | Ibid. Additionally provided heat sinks with rounded edges. | 2 |
| T5 Camera temperature | Active cooling system ensures low camera temperatures. | 2 | Passive cooling system (heat sinks) ensures low camera temperatures. | 2 |
| T6 Camera connectivity | Two cables. | 1 | Single cable (GigE connection). | 2 |
| T7 Light Source Energy | Xenon light source ensures sufficient illumination across VIS & NIR spectral ranges (250-1050 nm). | 2 | Ibid. | 2 |
| T8 Light Source Safety | 470-900 nm (VIS & NIR). | 2 | 665-975 nm (NIR). | 1 |
| T9 System mount | Not compatible with currently-available surgical supports. | 0 | Compatible with standard sterile mechanical arm systems. | 2 |
| T10 Camera Settings | Adjustments possible using software control. | 2 | Ibid. | 2 |
| T11 Focus | Optical system allows for manual focus for specific focal distance. | 1 | Ibid. | 1 |
| T12 Working distance (WD) | System design using scope and adjustable lenses allows imaging distances between 250-750 mm. | 2 | Ibid. | 2 |
| T13 Field of View | Optical system allows for 50 mm FOV at fixed WD of 250 mm. | 1 | Ibid. | 1 |
| T14 Depth of Field | Optical system allows for 35 mm DOF for 50 mm FOV at fixed WD of 250 mm. | 1 | Ibid. | 1 |
| T15 Spectral bands | 150 + bands. | 2 | 25 bands with 5 × 5 mosaic. | 1 |
| T16 Spectral Range | 470-900 nm (VIS & NIR). | 2 | 665-975 nm (NIR) | 1 |
| T17 Spatial Image Definition | 3650 × 2048 pixels. | 2 | 2048 × 1088 pixels with 5 × 5 mosaic, i.e. 409 × 217 pixels per band. | 1 |
| T18 Image Calibration | Image calibration for specific camera/light settings based on white and dark reference images (dark reference is automatically acquired). | 1 | Image calibration for specific camera/light settings based on white and dark reference images. | 1 |
| T19 Imaging Rate | 2-40 s per image. | 0 | 50 FPS. | 2 |

Various further modifications to the above described examples, whether by way of addition, deletion or substitution, will be apparent to the skilled person to provide additional examples, any and all of which are intended to be encompassed by the appended claims.

REFERENCES CITED

[1] I. J. Gerard, M. Kersten-Oertel, K. Petrecca, D. Sirhan, J. A. Hall, and D. L. Collins, "Brain shift in neuronavigation of brain tumors: A review," *Medical Image Analysis*, vol. 35, pp. 403-420, January 2017. [Online]. Available: http://dx.doi.org/10.1016/j.media.2016.08.007 https://linkinghub.elsevier.com/retrieve/pii/ S1361841516301566

[2] P. A. Helm, R. Teichman, S. L. Hartmann, and D. Simon, "Spinal Navigation and Imaging: History, Trends, and Future," *IEEE Transactions on Medical Imaging*, vol. 34, no. 8, pp. 1738-1746, August 2015. [Online]. Available: http://ieeexplore.ieee.org/document/7008544/[3]

[3] G. Lu and B. Fei, "Medical hyperspectral imaging: a review," *Journal of Biomedical Optics*, vol. 19, no. 1, p. 010901, January 2014. [Online]. Available: http://biomedicaloptics.spiedigitallibrary.org/article.aspx-?doi=10.1117/1330.19.1.010901

[4] M. Halicek, H. Fabelo, S. Ortega, G. M. Callico, and B. Fei, "In-Vivo and Ex-Vivo Tissue Analysis through Hyperspectral Imaging Techniques: Revealing the Invisible Features of Cancer," *Cancers*, vol. 11, no. 6, p. 756, May 2019. [Online]. Available: https://www.mdpi.com/ 2072-6694/11/6/756

[5] J. Shapey, Y. Xie, E. Nabavi, R. Bradford, S. R. Saeed, S. Ourselin, and T. Vercauteren, "Intraoperative multispectral and hyperspectral label-free imaging: A systematic review of in vivo clinical studies," *Journal of Biophotonics*, vol. 12, no. 9, p. e201800455, September 2019. [Online]. Available: https://onlinelibrary.wiley.com/doi/ abs/10.1002/jbio.201800455

[6] N. T. Clancy, G. Jones, L. Maier-Hein, D. S. Elson, and D. Stoyanov, "Surgical spectral imaging," *Medical Image Analysis*, vol. 63, p. 101699, 2020. [Online]. Available: https://doi.org/10.1016/j.media.2020.101699

[7] J. H. G. M. Klaessens, M. Nelisse, R. M. Verdaasdonk, and H. J. Noordmans, "Non-contact tissue perfusion and oxygenation imaging using a LED based multispectral and a thermal imaging system, first results of clinical intervention studies," in *Advanced Biomedical and Clinical Diagnostic Systems XI*, A. Mahadevan-Jansen, T. Vo-Dinh, and W. S. Grundfest, Eds., vol. 8572, March 2013, p. 857207. [Online]. Available: http://proceedings.spiedigitallibrary.org/proceeding.aspx?doi=10.1117/12.2003807

[8] M. Mori, T. Chiba, A. Nakamizo, R. Kumashiro, M. Murata, T. Akahoshi, M. Tomikawa, Y. Kikkawa, K. Yoshimoto, M. Mizoguchi, T. Sasaki, and M. Hashizume, "Intraoperative visualization of cerebral oxygenation using hyperspectral image data: a two-dimensional mapping method," *International Journal of Computer Assisted Radiology and Surgery*, vol. 9, no. 6, pp. 1059-1072, November 2014. [Online]. Available: http://link.springer.com/10.1007/s11548-014-0989-9

[9] E. Kho, L. L. de Boer, K. K. Van de Vijver, F. van Duijnhoven, M.-J. T. Vrancken Peeters, H. J. Sterenborg, and T. J. Ruers, "Hyperspectral Imaging for Resection Margin Assessment during Cancer Surgery," *Clinical Cancer Research*, vol. 25, no. 12, pp. 3572-3580, June 2019. [Online]. Available: http://clincancerres.aacrjournals.org/lookup/doi/10.1158/1078-0432.CCR-18-2089

[10] H. Fabelo, S. Ortega, R. Lazcano, D. Madroñal, G. M. Callicó, E. Juárez, R. Salvador, D. Bulters, H. Bulstrode, A. Szolna, J. Piñeiro, C. Sosa, A. J. O'Shanahan, S. Bisshopp, M. Hernandez, J. Morera, D. Ravi, B. Kiran, A. Vega, A. Báez-Quevedo, G.-Z. Yang, B. Stanciulescu, and R. Sarmiento, "An Intraoperative Visualization System Using Hyperspectral Imaging to Aid in Brain Tumor Delineation," *Sensors*, vol. 18, no. 2, p. 430, February 2018. [Online]. Available: http://www.mdpi.com/1424-8220/18/2/430

[11] N. Chiang, J. K. Jain, J. Sleigh, and T. Vasudevan, "Evaluation of hyperspectral imaging technology in patients with peripheral vascular disease," *Journal of Vascular Surgery*, vol. 66, no. 4, pp. 1192-1201, October 2017. [Online]. Available: http://dx.doi.org/10.1016/j.jvs.2017.02.047 https://linkinghub.elsevier.com/retrieve/pii/S0741521417309308

[12] M. Desjardins, J.-P. Sylvestre, R. Jafari, S. Kulasekara, K. Rose, R. Trussart, J. D. Arbour, C. Hudson, and F. Lesage, "Preliminary investigation of multispectral retinal tissue oximetry mapping using a hyperspectral retinal camera," *Experimental Eye Research*, vol. 146, pp. 330-340, May 2016. [Online]. Available: https://linkinghub.elsevier.com/retrieve/pii/S0014483516300653

[13] L. C. Cancio, A. I. Batchinsky, J. R. Mansfield, S. Panasyuk, K. Hetz, D. Martini, B. S. Jordan, B. Tracey, and J. E. Freeman, "Hyperspectral Imaging: A New Approach to the Diagnosis of Hemorrhagic Shock," *The Journal of Trauma: Injury, Infection, and Critical Care*, vol. 60, no. 5, pp. 1087-1095, May 2006. [Online]. Available: http://journals.lww.com/00005373-200605000-00025

[14] L. Khaodhiar, T. Dinh, K. T. Schomacker, S. V. Panasyuk, J. E. Freeman, R. Lew, T. Vo, A. A. Panasyuk, C. Lima, J. M. Giurini, T. E. Lyons, and A. Veves, "The Use of Medical Hyperspectral Technology to Evaluate Microcirculatory Changes in Diabetic Foot Ulcers and to Predict Clinical Outcomes," *Diabetes Care*, vol. 30, no. 4, pp. 903-910, April 2007. [Online]. Available: http://care.diabetesjournals.org/cgi/doi/10.2337/dc06-2209

[15] B. Fei, G. Lu, X. Wang, H. Zhang, J. V. Little, M. R. Patel, C. C. Griffith, M. W. El-Diery, and A. Y. Chen, "Label-free reflectance hyperspectral imaging for tumor margin assessment: a pilot study on surgical specimens of cancer patients," *Journal of Biomedical Optics*, vol. 22, no. 08, p. 1, August 2017. [Online]. Available: https://www.spiedigitallibrary.org/journals/journal-of-biomedical-optics/volume-22/issue-08/086009/La bel-free-reflectance-hyperspectral-imaging-for-tumor-margin-assessment/10.1117/1.JBO.22.8.086009.full

[16] H. Fabelo, M. Halicek, S. Ortega, M. Shahedi, A. Szolna, J. Piñeiro, C. Sosa, A. O'Shanahan, S. Bisshopp, C. Espino, M. Mârquez, M. Hernândez, D. Carrera, J. Morera, G. Callico, R. Sarmiento, and B. Fei, "Deep Learning-Based Framework for In Vivo Identification of Glioblastoma Tumor using Hyperspectral Images of Human Brain," *Sensors*, vol. 19, no. 4, p. 920, February 2019. [Online]. Available: http://www.mdpi.com/1424-8220/19/4/920

[17] S. Gioux, A. Mazhar, B. T. Lee, S. J. Lin, A. M. Tobias, D. J. Cuccia, A. Stockdale, R. Oketokoun, Y. Ashitate, E. Kelly, M. Weinmann, N. J. Durr, L. A. Moffitt, A. J. Durkin, B. J. Tromberg, and J. V. Frangioni, "First-in-human pilot study of a spatial frequency domain oxygenation imaging system," *Journal of Biomedical Optics, vol. 16, no. 8, p. 086015, 2011. [Online]. Available: http://biomedicaloptics.spiedigitallibrary.org/article.aspx?doi=10.1117/1.3614566

[18] S. L. Best, A. Thapa, N. Jackson, E. Olweny, M. Holzer, S. Park, E. Wehner, K. Zuzak, and J. A. Cadeddu, "Renal Oxygenation Measurement During Partial Nephrectomy Using Hyperspectral Imaging May Predict Acute Postoperative Renal Function," *Journal of Endourology*, vol. 27, no. 8, pp. 1037-1040, August 2013. [Online]. Available: http://www.liebertpub.com/doi/10.1089/end.2012.0683

[19] H. J. Noordmans, C. Ferrier, R. de Roode, F. Leijten, P. van Rijen, P. Gosselaar, J. Klaessens, and R. Verdaasdonk, "Imaging the seizure during surgery with a hyperspectral camera," *Epilepsia*, vol. 54, no. 11, pp. e150-e154, November 2013. [Online]. Available: http://doi.wiley.com/10.1111/epi.12386

[20] M. Barberio, F. Longo, C. Fiorillo, B. Seeliger, P. Mascagni, V. Agnus, V. Lindner, B. Geny, A.-L. Charles, I. Gockel, M. Worreth, A. Saadi, J. Marescaux, and M. Diana, "HYPerspectral Enhanced Reality (HYPER): a physiology-based surgical guidance tool," *Surgical Endoscopy*, vol. 34, no. 4, pp. 1736-1744, April 2020. [Online]. Available: https://doi.org/10.1007/s00464-019-06959-9 http://link.springer.com/10.1007/s00464-019-06959-9

[21] J. Yoon, J. Joseph, D. J. Waterhouse, A. S. Luthman, G. S. D. Gordon, M. di Pietro, W. Januszewicz, R. C. Fitzgerald, and S. E. Bohndiek, "A clinically translatable hyperspectral endoscopy (HySE) system for imaging the gastrointestinal tract," *Nature Communications*, vol. 10, no. 1, p. 1902, December 2019. [Online]. Available: http://dx.doi.org/10.1038/s41467-019-09484-4 http://www.nature.com/articles/s41467-019-09484-4

[22] R. Mühle, H. Ernst, S. B. Sobottka, and U. Morgenstern, "Workflow and hardware for intraoperative hyperspectral data acquisition in neurosurgery," *Biomedical Engineering/Biomedizinische Technik*, July 2020. [Online]. Available: https://www.degruyter.com/view/journals/bmte/ahead-of-print/article-10.1515-bmt-2019-0333/article-10.1515-bmt-2019-0333.xml

[23] A. Kulcke, A. Holmer, P. Wahl, F. Siemers, T. Wild, and G. Daeschlein, "A compact hyperspectral camera for measurement of perfusion parameters in medicine," *Biomedical Engineering/Biomedizinische Technik*, vol. 63, no. 5, pp. 519-527, October 2018. [Online]. Available: http://www.degruyter.com/view/j/bmte.2018.63.issue-5/bmt-2017-0145/bmt-2017-0145.xml

[24] H. Köhler, A. Kulcke, M. Maktabi, Y. Moulla, B. Jansen-Winkeln, M. Barberio, M. Diana, I. Gockel, T. Neumuth, and C. Chalopin, "Laparoscopic system for simultaneous high-resolution video and rapid hyperspectral imaging in the visible and near-infrared spectral range," *Journal of Biomedical Optics*, vol. 25, no. 08, August 2020. [Online]. Available: https://www.spiedigitallibrary.org/journals/journal-of-biomedical-optics/volume-25/issue-08/086004/Laparoscopic-system-for-simultaneous-high-resolution-video-and-rapid-hyperspectral/10.1117/1330.25.8.086004.full

[25] J. Pichette, A. Laurence, L. Angulo, F. Lesage, A. Bouthillier, D. K. Nguyen, and F. Leblond, "Intraoperative video-rate hemodynamic response assessment in human cortex using snapshot hyperspectral optical imaging," *Neurophotonics*, vol. 3, no. 4, p. 045003, October 2016. [Online]. Available: http://neurophotonics.spiedigitallibrary.org/article.aspx?doi=10.1117/1.NPh.3.4.045003

[26] M. Ewerlöf, M. Larsson, and E. G. Salerud, "Spatial and temporal skin blood volume and saturation estimation using a multispectral snapshot imaging camera," in *Imaging, Manipulation, and Analysis of Biomolecules, Cells, and Tissues XV*, D. L. Farkas, D. V. Nicolau, and R. C. Leif, Eds., vol. 10068, February 2017, p. 1006814. [Online]. Available: http://proceedings.spiedigitallibrary.org/proceeding.aspx?doi=10.1117/12.2251928

[27] K. Dijkstra, J. van de Loosdrecht, L. R. B. Schomaker, and M. A. Wiering, "Hyperspectral demosaicking and crosstalk correction using deep learning," *Machine Vision and Applications*, vol. 30, no. 1, pp. 1-21, February 2019. [Online]. Available: https://doi.org/10.1007/s00138-018-0965-4 http://link.springer.com/10.1007/s00138-018-0965-4

[28] G. Tsagkatakis, M. Bloemen, B. Geelen, M. Jayapala, and P. Tsakalides, "Graph and Rank Regularized Matrix Recovery for Snapshot Spectral Image Demosaicing," *IEEE Transactions on Computational Imaging*, vol. 5, no. 2, pp. 301-316, June 2019. [Online]. Available: https://ieeexplore.ieee.org/document/8584100/

[29] J. Shapey, Y. Xie, E. Nabavi, D. Ravi, S. R. Saeed, R. Bradford, S. Ourselin, and T. Vercauteren, "Towards intraoperative hyperspectral imaging: design considerations for neurosurgical applications," *Proceedings of Hamlyn Symposium on Medical Robotics*, p. 18, 2018.

[30] L. Ricciardi, K. L. Chaichana, A. Cardia, V. Stifano, Z. Rossini, A. Olivi, and C. L. Sturiale, "The Exoscope in Neurosurgery: An Innovative "Point of View". A Systematic Review of the Technical, Surgical, and Educational Aspects," *World Neurosurgery*, vol. 124, pp. 136-144, April 2019. [Online]. Available: https://doi.org/10.1016/j.wneu.2018.12.202 https://linkinghub.elsevier.com/retrieve/pii/S1878875019300804

[31] P. G. Yock, S. Zenios, J. Makower, T. J. Brinton, U. N. Kumar, F. T. J. Watkins, L. Denend, T. M. Krummel, and C. Q. Kurihara, *Biodesign: The process of innovating medical technologies*, 2nd ed. Cambridge University Press, 2015.

[32] S. H. Yun and S. J. J. Kwok, "Light in diagnosis, therapy and surgery," *Nature Biomedical Engineering*, vol. 1, no. 1, p. 0008, January 2017. [Online]. Available: http://www.nature.com/articles/s41551-016-0008

[33] K. Nishiyama, "From Exoscope into the Next Generation," *Journal of Korean Neurosurgical Society*, vol. 60, no. 3, pp. 289-293, May 2017. [Online]. Available: http://jkns.or.kr/journal/view.php?doi=10.3340/jkns.2017.0202.003

[34] D. J. Langer, T. G. White, M. Schulder, J. A. Boockvar, M. Labib, and M. T. Lawton, "Advances in Intraoperative Optics: A Brief Review of Current Exoscope Platforms," *Operative Neurosurgery*, vol. 19, no. 1, pp. 84-93, July 2020. [Online]. Available: https://academic.oup.com/ons/article/19/1/84/5569799

[35] S. Thorpe, D. Fize, and C. Marlot, "Speed of processing in the human visual system," *Nature*, vol. 381, no. 6582, pp. 520-522, June 1996. [Online]. Available: http://www.nature.com/articles/381520a0

[36] P. C. Cotterill, J. P. Kostuik, G. D'Angelo, G. R. Fernie, and B. E. Maki, "An anatomical comparison of the human and bovine thoracolumbar spine," *Journal of Orthopaedic Research*, vol. 4, no. 3, pp. 298-303, 1986. [Online]. Available: http://doi.wiley.com/10.1002/jor.1100040306

[37] A. Myronenko and X. Song, "Point Set Registration: Coherent Point Drift," *IEEE Transactions on Pattern Analysis and Machine Intelligence*, vol. 32, no. 12, pp. 2262-2275, December 2010. [Online]. Available: http://arxiv.org/abs/0905.2635%0Ahttp://dx.doi.org/10.1109/TPAMI.2010.46 http://ieeexplore.ieee.org/document/5432191/

[38] J. Schwiegerling, C. Chancy, and R. C. Dimalanta, "Depth of Focus Measurement of an Ophthalmic Surgical Microscope," *Investigative Ophthalmology & Visual Science*, vol. 56, no. 7, p. 1925, 2015.

[39] L. Ayala, S. Seidlitz, A. Vemuri, S. J. Wirkert, T. Kirchner, T. J. Adler, C. Engels, D. Teber, and L. Maier-Hein, "Light source calibration for multispectral imaging in surgery," *International Journal of Computer Assisted Radiology and Surgery*, vol. 15, no. 7, pp. 1117-1125, July 2020. [Online]. Available: https://doi.org/10.1007/s11548-020-02195-y http://link.springer.com/10.1007/s11548-020-02195-y

The invention claimed is:

1. A method of determining parameters of a desired target image from hyperspectral imagery obtained from a surgical procedure, comprising:

capturing in real time hyperspectral snapshot mosaic images of a scene from the surgical procedure using a hyperspectral image sensor coupled to an optical scope, the snapshot mosaic images being of relatively low spatial and low spectral resolution;

undertaking spatio-spectrally aware demosaicking of the snapshot mosaic images, the demosaicking comprising an algorithm to optimise for a cost function accounting for spatial crosstalk across neighbouring pixels corresponding to different spectral bands in the snapshot mosaic image, upsampling of the snapshot mosaic images, and the application of a spectral calibration operator, to generate a virtual hypercube of the snapshot mosaic image data, the virtual hypercube comprising image data of relatively high spatial resolution compared to the snapshot mosaic images;

from the image data in the virtual hypercube, determining relatively high spatial resolution parameters of a desired target image; and outputting in real time the determined relatively high-resolution parameters as representative of the desired target image.

2. A method according to claim 1, wherein the demosaicking comprises machine learning.

3. A method according to claim 1, wherein the demosaicking is temporally consistent between two or more consecutive frames based on motion compensation in between frames.

4. A method according to claim 1, and further comprising, prior to capturing the hyperspectral snapshot mosaic images, undertaking a white balancing operation on the hyperspectral image sensor.

5. A method according to claim 4, wherein the white balancing operation comprises separately acquiring reference images, including dark and white reference mosaic images $w_{d;\tau_d}$ and $w_{w;\tau_w}$ at integration times $\tau_d$ and $\tau_w$, respectively, and deploying a linear model where in addition to the acquired mosaic image $w_\tau$ of an object with integration time $\tau$, a white reference mosaic image $w_{w;\tau_w}$ of a reflectance tile with integration time $\tau_w$, and dark reference mosaic images $w_{d;\tau}$ and $w_{d;\tau_w}$ are acquired with integration times $\tau$ and $\tau_w$, with a closed shutter, and the white balancing operation yields a reflectance mosaic image given by $$r := \frac{w_\tau - w_{d;\tau}}{w_{w;\tau_w} - w_{d;\tau_w}} \frac{\tau_w}{\tau} \in W.$$

6. A method according to claim 1, and further comprising, prior to capturing the hyperspectral snapshot mosaic images, undertaking a spatiospectral calibration operation on the hyperspectral image sensor.

7. A method according to claim 6, wherein a real spectral filter response operator $B_F: \mathbb{R}^{n_A} \to \mathbb{R}^{m_1 m_2}$ and a spatial cross-talk operator T: W→W are estimated in a controlled setup to account for parasitical effects during image acquisition.

8. A method according to claim 7, and further comprising measuring a characteristic of the hyperspectral image sensor to obtain a measured system filter response operator $A_F^{meas}$: U→W by acquiring snapshot mosaic image data using collimated light and sweeping through all wavelengths in conjunction with an imaging target with known, typically spatially-constant, spectral signature.

9. A method according to claim 1, wherein the determining of the relatively high spatial parameters further comprises analysing pixel-level hyperspectral information for its composition of unique end-members characterised by specific spectral signatures.

10. A method according to claim 1, wherein the determining of the relatively high spatial parameters further comprises estimation of tissue properties per spatial location (typically pixels) from reflectance information of hyperspectral imaging, such as pixel-level tissue absorption information.

11. A method of determining parameters of a desired target image from hyperspectral imagery, comprising:
    capturing in real time hyperspectral snapshot mosaic images of a scene from a surgical procedure using a hyperspectral image sensor coupled to an optical scope, the snapshot mosaic images being of relatively low spatial and low spectral resolution;
    undertaking a joint demosaicking and parameter estimation from the snapshot mosaic images to determine relatively high spatial resolution parameters of a desired target image; and
    outputting in real time the determined relatively high-resolution parameters as representative of the desired target image,
    wherein the demosaicking is spatio-spectrally aware, and comprises an algorithm to optimise for a cost function accounting for spatial crosstalk across neighbouring pixels corresponding to different spectral bands in the snapshot mosaic image, upsampling of the snapshot mosaic images, and application of a spectral calibration operator.

12. A non-transitory computer readable storage medium storing a computer program that when executed causes a hyperspectral imaging system to perform a method comprising:
    capturing in real time hyperspectral snapshot mosaic images of a scene from a surgical procedure using a hyperspectral image sensor coupled to an optical scope, the snapshot mosaic images being of relatively low spatial and low spectral resolution;
    undertaking spatio-spectrally aware demosaicking of the snapshot mosaic images, the demosaicking comprising an algorithm to optimise for a cost function accounting for spatial crosstalk across neighbouring pixels corresponding to different spectral bands in the snapshot mosaic image, upsampling of the snapshot mosaic images, and the application of a spectral calibration operator, to generate a virtual hypercube of the snapshot mosaic image data, the virtual hypercube comprising image data of relatively high spatial resolution compared to the snapshot mosaic images;
    from the image data in the virtual hypercube, determining relatively high spatial resolution parameters of a desired target image; and
    outputting in real time the determined relatively high-resolution parameters as representative of the desired target image.

* * * * *